(12) United States Patent
Felix et al.

(10) Patent No.: US 9,642,537 B2
(45) Date of Patent: May 9, 2017

(54) AMBULATORY EXTENDED-WEAR ELECTROCARDIOGRAPHY AND SYNCOPE SENSOR MONITOR

(71) Applicant: Bardy Diagnostics, Inc., Vashon, WA (US)

(72) Inventors: Jason Felix, Vashon Island, WA (US); Jon Mikalson Bishay, Seattle, WA (US); Gust H. Bardy, Carnation, WA (US)

(73) Assignee: BARDY DIAGNOSTICS, INC., Charlotte, NC (US)

( * ) Notice: Subject to any disclaimer, the term of this patent is extended or adjusted under 35 U.S.C. 154(b) by 0 days.

(21) Appl. No.: 14/684,260

(22) Filed: Apr. 10, 2015

(65) Prior Publication Data

US 2016/0213263 A1 Jul. 28, 2016

Related U.S. Application Data

(63) Continuation-in-part of application No. 14/082,108, filed on Nov. 16, 2013, which is a
(Continued)

(51) Int. Cl.
*A61B 5/0205* (2006.01)
*A61B 5/00* (2006.01)
(Continued)

(52) U.S. Cl.
CPC ........ *A61B 5/02055* (2013.01); *A61B 5/0006* (2013.01); *A61B 5/0022* (2013.01);
(Continued)

(58) Field of Classification Search
CPC .................. A61B 5/02055; A61B 5/04325
See application file for complete search history.

(56) References Cited

U.S. PATENT DOCUMENTS 3,215,136 A 11/1965 Holter et al.
3,699,948 A 10/1972 Ota et al.
(Continued)

FOREIGN PATENT DOCUMENTS

DE 19955211 5/2001
EP 1859833 11/2007
(Continued)

OTHER PUBLICATIONS

US 6,527,714, 03/2003, Bardy (withdrawn)
(Continued)

*Primary Examiner* — William Thomson
*Assistant Examiner* — Amanda Steinberg
(74) *Attorney, Agent, or Firm* — Patrick J. S. Inouye; Leonid Kisselev

(57) ABSTRACT

Physiological monitoring can be provided through a syncope sensor imbedded into an electrocardiography monitor, which correlates syncope events and electrocardiographic data. Physiological monitoring can be provided through a lightweight wearable monitor that includes two components, a flexible extended-wear electrode patch and a reusable monitor recorder that removably snaps into a receptacle on the electrode patch. The wearable monitor sits centrally on the patient's chest at the sternal midline and includes a unique narrow "hourglass"-like shape, significantly improving the ability of the monitor to cutaneously sense cardiac electrical potential signals, particularly the P-wave and QRS interval signals, which indicate ventricular activity in electrocardiographic waveforms. The electrocardiographic electrodes on the electrode patch are tailored for axial positioning along the midline of the sternum to capture action potential propagation in an orientation that corresponds to the aVF lead in a conventional 12-lead electrocardiogram, which senses positive P-waves.

20 Claims, 20 Drawing Sheets

Related U.S. Application Data continuation-in-part of application No. 14/080,717, filed on Nov. 14, 2013, now Pat. No. 9,545,204, and a continuation-in-part of application No. 14/080,725, filed on Nov. 14, 2013, application No. 14/684,260, which is a continuation-in-part of application No. 14/488,230, filed on Sep. 16, 2014, which is a continuation-in-part of application No. 14/080,725.

(60) Provisional application No. 61/882,403, filed on Sep. 25, 2013.

(51) Int. Cl.
| | |
|---|---|
| A61B 5/04 | (2006.01) |
| A61B 5/0408 | (2006.01) |
| A61B 5/0432 | (2006.01) |
| A61B 5/0452 | (2006.01) |
| A61B 5/11 | (2006.01) |
| A61B 5/01 | (2006.01) |
| A61B 5/021 | (2006.01) |
| A61B 5/087 | (2006.01) |
| A61B 5/091 | (2006.01) |
| A61B 5/145 | (2006.01) |
| A61B 5/1455 | (2006.01) |
| G01N 27/30 | (2006.01) |

(52) U.S. Cl.
CPC ........ *A61B 5/04017* (2013.01); *A61B 5/0452* (2013.01); *A61B 5/04085* (2013.01); *A61B 5/04087* (2013.01); *A61B 5/04325* (2013.01); *A61B 5/04525* (2013.01); *A61B 5/1116* (2013.01); *A61B 5/1117* (2013.01); *A61B 5/1118* (2013.01); *A61B 5/4809* (2013.01); *A61B 5/6801* (2013.01); *A61B 5/6823* (2013.01); *A61B 5/6833* (2013.01); *A61B 5/01* (2013.01); *A61B 5/021* (2013.01); *A61B 5/087* (2013.01); *A61B 5/091* (2013.01); *A61B 5/14532* (2013.01); *A61B 5/14551* (2013.01); *A61B 5/7455* (2013.01); *A61B 2505/07* (2013.01); *A61B 2560/0271* (2013.01); *A61B 2560/045* (2013.01); *A61B 2560/0412* (2013.01); *A61B 2562/0219* (2013.01); *A61B 2562/164* (2013.01); *G01N 27/307* (2013.01)

(56) References Cited

U.S. PATENT DOCUMENTS

| | | | |
|---|---|---|---|
| 3,893,453 A | 7/1975 | Goldberg | |
| 4,123,785 A | 10/1978 | Cherry et al. | |
| 4,328,814 A | 5/1982 | Arkans | |
| 4,441,500 A | 4/1984 | Sessions et al. | |
| 4,532,934 A | 8/1985 | Kelen | |
| 4,550,502 A | 11/1985 | Grayzel | |
| 4,716,903 A | 1/1988 | Hansen | |
| 4,809,705 A | 3/1989 | Ascher | |
| 4,915,656 A | 4/1990 | Alferness | |
| 5,025,794 A | 6/1991 | Albert et al. | |
| 5,168,876 A | 12/1992 | Quedens et al. | |
| 5,215,098 A | 6/1993 | Steinhaus | |
| D341,423 S | 11/1993 | Bible | |
| 5,265,579 A | 11/1993 | Ferrari | |
| 5,341,806 A | 8/1994 | Gadsby et al. | |
| 5,355,891 A | 10/1994 | Wateridge et al. | |
| 5,365,934 A | 11/1994 | Leon et al. | |
| 5,392,784 A | 2/1995 | Gudaitis | |
| D357,069 S | 4/1995 | Plahn et al. | |
| 5,402,780 A | 4/1995 | Faasse, Jr. | |
| 5,402,884 A | 4/1995 | Gilman et al. | |
| 5,450,845 A | 9/1995 | Axelgaard | |
| 5,458,141 A | 10/1995 | Neil | |
| 5,473,537 A | 12/1995 | Glazer et al. | |
| 5,483,969 A | 1/1996 | Testerman et al. | |
| 5,511,553 A | 4/1996 | Segalowitz | |
| 5,540,733 A | 7/1996 | Testerman et al. | |
| 5,546,952 A | 8/1996 | Erickson | |
| 5,549,655 A | 8/1996 | Erickson | |
| 5,579,919 A | 12/1996 | Gilman et al. | |
| 5,582,181 A | 12/1996 | Ruess | |
| D377,983 S | 2/1997 | Sabri et al. | |
| 5,601,089 A | 2/1997 | Bledsoe et al. | |
| 5,623,935 A | 4/1997 | Faisandier | |
| 5,682,901 A | 11/1997 | Kamen | |
| 5,697,955 A | 12/1997 | Stolte | |
| 5,749,902 A | 5/1998 | Olsen et al. | |
| 5,817,151 A | 10/1998 | Olsen et al. | |
| 5,819,741 A | 10/1998 | Karlsson et al. | |
| 5,850,920 A | 12/1998 | Gilman et al. | |
| D407,159 S | 3/1999 | Roberg | |
| 5,876,351 A | 3/1999 | Rohde | |
| 5,906,583 A | 5/1999 | Rogel | |
| 5,951,598 A | 9/1999 | Bishay et al. | |
| 5,957,857 A | 9/1999 | Hartley | |
| 5,984,102 A | 11/1999 | Tay | |
| 6,032,064 A | 2/2000 | Devlin et al. | |
| 6,038,469 A | 3/2000 | Karlsson et al. | |
| 6,101,413 A | 8/2000 | Olsen et al. | |
| 6,115,638 A | 9/2000 | Groenke | |
| 6,117,077 A | 9/2000 | Del Mar et al. | |
| 6,134,479 A | 10/2000 | Brewer et al. | |
| 6,148,233 A | 11/2000 | Owen et al. | |
| 6,149,602 A | 11/2000 | Arcelus | |
| 6,149,781 A | 11/2000 | Forand | |
| 6,188,407 B1 | 2/2001 | Smith et al. | |
| D443,063 S | 5/2001 | Pisani et al. | |
| 6,245,025 B1 | 6/2001 | Torok et al. | |
| 6,246,330 B1 | 6/2001 | Nielsen | |
| D445,507 S | 7/2001 | Pisani et al. | |
| 6,269,267 B1 | 7/2001 | Bardy et al. | |
| 6,272,385 B1 | 8/2001 | Bishay et al. | |
| 6,298,255 B1 | 10/2001 | Cordero et al. | |
| 6,301,502 B1 | 10/2001 | Owen et al. | |
| 6,304,773 B1 | 10/2001 | Taylor et al. | |
| 6,304,780 B1 | 10/2001 | Owen et al. | |
| 6,304,783 B1 | 10/2001 | Lyster et al. | |
| 6,374,138 B1 | 4/2002 | Owen et al. | |
| 6,416,471 B1 * | 7/2002 | Kumar | G06F 19/323 128/903 |
| 6,418,342 B1 | 7/2002 | Owen et al. | |
| 6,424,860 B1 | 7/2002 | Karlsson et al. | |
| 6,427,083 B1 | 7/2002 | Owen et al. | |
| 6,456,872 B1 | 9/2002 | Faisandier | |
| 6,463,320 B1 | 10/2002 | Xue et al. | |
| 6,546,285 B1 | 4/2003 | Owen et al. | |
| 6,605,046 B1 | 8/2003 | Del Mar | |
| 6,607,485 B2 | 8/2003 | Bardy | |
| 6,611,705 B2 | 8/2003 | Hopman et al. | |
| 6,671,545 B2 | 12/2003 | Fincke | |
| 6,671,547 B2 | 12/2003 | Lyster et al. | |
| 6,694,186 B2 | 2/2004 | Bardy | |
| 6,704,595 B2 | 3/2004 | Bardy | |
| 6,705,991 B2 | 3/2004 | Bardy | |
| 6,719,701 B2 | 4/2004 | Lade | |
| 6,754,523 B2 | 6/2004 | Toole | |
| 6,782,293 B2 | 8/2004 | Dupelle et al. | |
| 6,856,832 B1 | 2/2005 | Matsumura et al. | |
| 6,860,897 B2 | 3/2005 | Bardy | |
| 6,866,629 B2 | 3/2005 | Bardy | |
| 6,887,201 B2 | 5/2005 | Bardy | |
| 6,893,397 B2 | 5/2005 | Bardy | |
| 6,904,312 B2 | 6/2005 | Bardy | |
| 6,908,431 B2 | 6/2005 | Bardy | |
| 6,913,577 B2 | 7/2005 | Bardy | |
| 6,944,498 B2 | 9/2005 | Owen et al. | |
| 6,960,167 B2 | 11/2005 | Bardy | |
| 6,970,731 B1 | 11/2005 | Jayaraman et al. | |
| 6,978,169 B1 | 12/2005 | Guerra | |
| 6,993,377 B2 | 1/2006 | Flick et al. | |
| 7,020,508 B2 | 3/2006 | Stivoric et al. | |
| 7,027,864 B2 | 4/2006 | Snyder et al. | |

(56) References Cited

U.S. PATENT DOCUMENTS

| | | |
|---|---|---|
| 7,065,401 B2 | 6/2006 | Worden |
| 7,085,601 B1 | 8/2006 | Bardy et al. |
| 7,104,955 B2 | 9/2006 | Bardy |
| 7,134,996 B2 | 11/2006 | Bardy |
| 7,137,389 B2 | 11/2006 | Berthon-Jones |
| 7,147,600 B2 | 12/2006 | Bardy |
| 7,215,991 B2 | 5/2007 | Besson et al. |
| 7,248,916 B2 | 7/2007 | Bardy |
| 7,257,438 B2 | 8/2007 | Kinast |
| 7,277,752 B2 | 10/2007 | Matos |
| D558,882 S | 1/2008 | Brady |
| 7,328,061 B2 | 2/2008 | Rowlandson et al. |
| 7,412,395 B2 | 8/2008 | Rowlandson et al. |
| 7,429,938 B1 | 9/2008 | Corndorf |
| 7,552,031 B2 | 6/2009 | Vock et al. |
| D606,656 S | 12/2009 | Kobayashi et al. |
| 7,706,870 B2 | 4/2010 | Shieh et al. |
| 7,756,721 B1 | 7/2010 | Falchuk et al. |
| 7,787,943 B2 | 8/2010 | McDonough |
| 7,874,993 B2 | 1/2011 | Bardy |
| 7,881,785 B2 | 2/2011 | Nassif et al. |
| D639,437 S | 6/2011 | Bishay et al. |
| 7,959,574 B2 | 6/2011 | Bardy |
| 8,116,841 B2 | 2/2012 | Bly et al. |
| 8,150,502 B2 | 4/2012 | Kumar et al. |
| 8,160,682 B2 | 4/2012 | Kumar et al. |
| 8,172,761 B1 | 5/2012 | Rulkov et al. |
| 8,180,425 B2 | 5/2012 | Selvitelli et al. |
| 8,200,320 B2 | 6/2012 | Kovacs |
| 8,231,539 B2 | 7/2012 | Bardy |
| 8,231,540 B2 | 7/2012 | Bardy |
| 8,239,012 B2 | 8/2012 | Felix et al. |
| 8,249,686 B2 | 8/2012 | Libbus et al. |
| 8,260,414 B2 | 9/2012 | Nassif et al. |
| 8,266,008 B1 | 9/2012 | Siegal et al. |
| 8,277,378 B2 | 10/2012 | Bardy |
| 8,285,356 B2 | 10/2012 | Bly et al. |
| 8,285,370 B2 | 10/2012 | Felix et al. |
| 8,308,650 B2 | 11/2012 | Bardy |
| 8,366,629 B2 | 2/2013 | Bardy |
| 8,374,688 B2 | 2/2013 | Libbus et al. |
| 8,412,317 B2 | 4/2013 | Mazar |
| 8,460,189 B2 | 6/2013 | Libbus et al. |
| 8,473,047 B2 | 6/2013 | Chakravarthy et al. |
| 8,478,418 B2 | 7/2013 | Fahey |
| 8,554,311 B2 | 10/2013 | Warner et al. |
| 8,591,430 B2 | 11/2013 | Amurthur et al. |
| 8,594,763 B1 | 11/2013 | Bibian et al. |
| 8,600,486 B2 | 12/2013 | Kaib et al. |
| 8,613,708 B2 | 12/2013 | Bishay et al. |
| 8,613,709 B2 | 12/2013 | Bishay et al. |
| 8,620,418 B1 | 12/2013 | Kuppuraj et al. |
| 8,626,277 B2 | 1/2014 | Felix et al. |
| 8,684,925 B2 | 4/2014 | Manicka et al. |
| 8,688,190 B2 | 4/2014 | Libbus et al. |
| 8,718,752 B2 | 5/2014 | Libbus et al. |
| 8,744,561 B2 | 6/2014 | Fahey |
| 8,774,932 B2 | 7/2014 | Fahey |
| 8,790,257 B2 | 7/2014 | Libbus et al. |
| 8,790,259 B2 | 7/2014 | Katra et al. |
| 8,795,174 B2 | 8/2014 | Manicka et al. |
| 8,798,729 B2 | 8/2014 | Kaib et al. |
| 8,798,734 B2 | 8/2014 | Kuppuraj et al. |
| 8,818,478 B2 | 8/2014 | Scheffler et al. |
| 8,818,481 B2 | 8/2014 | Bly et al. |
| 8,823,490 B2 | 9/2014 | Libbus et al. |
| 8,938,287 B2 | 1/2015 | Felix et al. |
| 8,965,492 B2 | 2/2015 | Baker et al. |
| 9,066,664 B2 | 6/2015 | Karjalainen |
| 9,155,484 B2 | 10/2015 | Baker et al. |
| 9,204,813 B2 | 12/2015 | Kaib et al. |
| 9,277,864 B2 | 3/2016 | Yang et al. |
| 9,339,202 B2 | 5/2016 | Brockway et al. |
| 2002/0013538 A1 | 1/2002 | Teller |
| 2002/0013717 A1 | 1/2002 | Ando et al. |
| 2002/0103422 A1 | 8/2002 | Harder et al. |
| 2002/0120310 A1 | 8/2002 | Linden et al. |
| 2002/0184055 A1 | 12/2002 | Naghavi et al. |
| 2002/0193668 A1 | 12/2002 | Munneke |
| 2003/0004547 A1 | 1/2003 | Owen et al. |
| 2003/0073916 A1 | 4/2003 | Yonce |
| 2003/0083559 A1 | 5/2003 | Thompson |
| 2003/0097078 A1 | 5/2003 | Maeda |
| 2003/0139785 A1 | 7/2003 | Riff et al. |
| 2003/0176802 A1 | 9/2003 | Galen et al. |
| 2003/0211797 A1 | 11/2003 | Hill et al. |
| 2004/0008123 A1 | 1/2004 | Carrender |
| 2004/0019288 A1 | 1/2004 | Kinast |
| 2004/0034284 A1 | 2/2004 | Aversano et al. |
| 2004/0049132 A1 | 3/2004 | Barron et al. |
| 2004/0073127 A1 | 4/2004 | Istvan et al. |
| 2004/0087836 A1 | 5/2004 | Green et al. |
| 2004/0093192 A1 | 5/2004 | Hasson et al. |
| 2004/0148194 A1 | 7/2004 | Wellons et al. |
| 2004/0207530 A1 | 10/2004 | Nielsen |
| 2004/0236202 A1 | 11/2004 | Burton |
| 2004/0243435 A1 | 12/2004 | Williams |
| 2004/0256453 A1 | 12/2004 | Lammle |
| 2004/0260188 A1 | 12/2004 | Syed et al. |
| 2004/0260192 A1 | 12/2004 | Yamamoto |
| 2005/0096717 A1 | 5/2005 | Bishay et al. |
| 2005/0108055 A1 | 5/2005 | Ott et al. |
| 2005/0154267 A1 | 7/2005 | Bardy |
| 2005/0182308 A1 | 8/2005 | Bardy |
| 2005/0182309 A1 | 8/2005 | Bardy |
| 2005/0215918 A1 | 9/2005 | Frantz et al. |
| 2005/0222513 A1 | 10/2005 | Hadley et al. |
| 2005/0228243 A1 | 10/2005 | Bardy |
| 2005/0245839 A1 | 11/2005 | Stivoric et al. |
| 2006/0025696 A1 | 2/2006 | Kurzweil et al. |
| 2006/0025824 A1 | 2/2006 | Freeman et al. |
| 2006/0030767 A1 | 2/2006 | Lang et al. |
| 2006/0041201 A1 | 2/2006 | Behbehani et al. |
| 2006/0122469 A1 | 6/2006 | Martel |
| 2006/0124193 A1 | 6/2006 | Orr et al. |
| 2006/0224072 A1 | 10/2006 | Shennib |
| 2006/0235320 A1 | 10/2006 | Tan et al. |
| 2006/0253006 A1 | 11/2006 | Bardy |
| 2006/0264730 A1 | 11/2006 | Stivoric et al. |
| 2007/0003115 A1 | 1/2007 | Patton et al. |
| 2007/0050209 A1 | 3/2007 | Yered |
| 2007/0078324 A1 | 4/2007 | Wijisiriwardana |
| 2007/0093719 A1 | 4/2007 | Nichols, Jr. et al. |
| 2007/0100248 A1 | 5/2007 | Van Dam et al. |
| 2007/0100667 A1 | 5/2007 | Bardy |
| 2007/0123801 A1 | 5/2007 | Goldberger et al. |
| 2007/0136091 A1 | 6/2007 | McTaggart |
| 2007/0179357 A1 | 8/2007 | Bardy |
| 2007/0185390 A1 | 8/2007 | Perkins et al. |
| 2007/0203415 A1 | 8/2007 | Bardy |
| 2007/0203423 A1 | 8/2007 | Bardy |
| 2007/0208232 A1 | 9/2007 | Kovacs |
| 2007/0208233 A1 | 9/2007 | Kovacs |
| 2007/0208266 A1 | 9/2007 | Hadley |
| 2007/0225611 A1* | 9/2007 | Kumar ............... A61B 5/0006 600/523 |
| 2007/0244405 A1 | 10/2007 | Xue et al. |
| 2007/0249946 A1 | 10/2007 | Kumar et al. |
| 2007/0255153 A1 | 11/2007 | Kumar et al. |
| 2007/0265510 A1 | 11/2007 | Bardy |
| 2007/0276270 A1 | 11/2007 | Tran |
| 2007/0276275 A1 | 11/2007 | Proctor et al. |
| 2007/0293738 A1 | 12/2007 | Bardy |
| 2007/0293739 A1 | 12/2007 | Bardy |
| 2007/0293740 A1 | 12/2007 | Bardy |
| 2007/0293741 A1 | 12/2007 | Bardy |
| 2007/0293772 A1 | 12/2007 | Bardy |
| 2007/0299325 A1 | 12/2007 | Farrell et al. |
| 2007/0299617 A1 | 12/2007 | Willis |
| 2008/0051668 A1 | 2/2008 | Bardy |
| 2008/0058661 A1 | 3/2008 | Bardy |
| 2008/0091097 A1 | 4/2008 | Linti et al. |
| 2008/0139953 A1 | 6/2008 | Baker et al. |
| 2008/0143080 A1 | 6/2008 | Burr |

(56) References Cited

U.S. PATENT DOCUMENTS

| | | |
|---|---|---|
| 2008/0177168 A1 | 7/2008 | Callahan et al. |
| 2008/0194927 A1 | 8/2008 | KenKnight et al. |
| 2008/0208009 A1 | 8/2008 | Shklarski |
| 2008/0208014 A1 | 8/2008 | KenKnight et al. |
| 2008/0284599 A1 | 11/2008 | Zdeblick et al. |
| 2008/0288026 A1 | 11/2008 | Cross et al. |
| 2008/0306359 A1 | 12/2008 | Zdeblick et al. |
| 2009/0054952 A1 | 2/2009 | Glukhovsky et al. |
| 2009/0062897 A1 | 3/2009 | Axelgaard |
| 2009/0069867 A1 | 3/2009 | KenKnight et al. |
| 2009/0073991 A1 | 3/2009 | Landrum et al. |
| 2009/0076336 A1 | 3/2009 | Mazar et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076346 A1 | 3/2009 | James et al. |
| 2009/0076349 A1 | 3/2009 | Libbus et al. |
| 2009/0076397 A1 | 3/2009 | Libbus et al. |
| 2009/0076401 A1 | 3/2009 | Mazar et al. |
| 2009/0076559 A1 | 3/2009 | Libbus et al. |
| 2009/0088652 A1 | 4/2009 | Tremblay |
| 2009/0112116 A1 | 4/2009 | Lee et al. |
| 2009/0131759 A1* | 5/2009 | Sims ............... A61B 5/1135 600/301 |
| 2009/0216132 A1 | 8/2009 | Orbach |
| 2009/0264792 A1 | 10/2009 | Mazar |
| 2009/0270708 A1 | 10/2009 | Shen et al. |
| 2009/0270747 A1 | 10/2009 | Van Dam et al. |
| 2009/0292194 A1 | 11/2009 | Libbus et al. |
| 2010/0007413 A1* | 1/2010 | Herleikson ........ A61B 5/0424 330/124 R |
| 2010/0022897 A1 | 1/2010 | Parker et al. |
| 2010/0056881 A1 | 3/2010 | Libbus et al. |
| 2010/0081913 A1 | 4/2010 | Cross et al. |
| 2010/0185063 A1 | 7/2010 | Bardy |
| 2010/0185076 A1 | 7/2010 | Jeong et al. |
| 2010/0191154 A1 | 7/2010 | Berger et al. |
| 2010/0191310 A1 | 7/2010 | Bly |
| 2010/0234715 A1 | 9/2010 | Shin et al. |
| 2010/0234716 A1 | 9/2010 | Engel |
| 2010/0280366 A1 | 11/2010 | Arne et al. |
| 2010/0324384 A1 | 12/2010 | Moon et al. |
| 2011/0054286 A1 | 3/2011 | Crosby et al. |
| 2011/0066041 A1 | 3/2011 | Pandia et al. |
| 2011/0077497 A1 | 3/2011 | Oster et al. |
| 2011/0144470 A1 | 6/2011 | Mazar et al. |
| 2011/0160548 A1 | 6/2011 | Forster et al. |
| 2011/0224564 A1 | 9/2011 | Moon et al. |
| 2011/0237924 A1 | 9/2011 | McGusty et al. |
| 2011/0245699 A1 | 10/2011 | Snell et al. |
| 2011/0245711 A1* | 10/2011 | Katra ............... A61B 5/0537 600/547 |
| 2012/0003933 A1 | 1/2012 | Baker et al. |
| 2012/0029306 A1 | 2/2012 | Paquet et al. |
| 2012/0029316 A1* | 2/2012 | Raptis .............. A61B 5/0002 600/301 |
| 2012/0035432 A1 | 2/2012 | Katra et al. |
| 2012/0088998 A1 | 4/2012 | Bardy et al. |
| 2012/0088999 A1 | 4/2012 | Bishay et al. |
| 2012/0089000 A1 | 4/2012 | Bishay et al. |
| 2012/0089001 A1 | 4/2012 | Bishay et al. |
| 2012/0089037 A1 | 4/2012 | Bishay et al. |
| 2012/0089412 A1 | 4/2012 | Bardy et al. |
| 2012/0089417 A1 | 4/2012 | Bardy et al. |
| 2012/0095352 A1 | 4/2012 | Tran |
| 2012/0101358 A1 | 4/2012 | Boettcher et al. |
| 2012/0101396 A1* | 4/2012 | Solosko ............ A61B 5/0006 600/509 |
| 2012/0165645 A1 | 6/2012 | Russel et al. |
| 2012/0302906 A1 | 11/2012 | Felix et al. |
| 2012/0330126 A1 | 12/2012 | Hoppe et al. |
| 2013/0041272 A1 | 2/2013 | Guillen Arredondo et al. |
| 2013/0077263 A1 | 3/2013 | Oleson et al. |
| 2013/0079611 A1 | 3/2013 | Besko |
| 2013/0085403 A1 | 4/2013 | Gunderson et al. |
| 2013/0096395 A1 | 4/2013 | Katra et al. |
| 2013/0116533 A1 | 5/2013 | Lian et al. |
| 2013/0123651 A1 | 5/2013 | Bardy |
| 2013/0158361 A1 | 6/2013 | Bardy |
| 2013/0225963 A1 | 8/2013 | Kodandaramaiah et al. |
| 2013/0225966 A1 | 8/2013 | Macia Barber et al. |
| 2013/0243105 A1 | 9/2013 | Lei et al. |
| 2013/0274584 A1* | 10/2013 | Finlay .............. A61B 5/0432 600/391 |
| 2013/0275158 A1 | 10/2013 | Fahey |
| 2013/0324809 A1 | 12/2013 | Lisogurski et al. |
| 2013/0324855 A1 | 12/2013 | Lisogurski et al. |
| 2013/0324856 A1 | 12/2013 | Lisogurski et al. |
| 2013/0325359 A1 | 12/2013 | Jarverud et al. |
| 2013/0331665 A1 | 12/2013 | Libbus et al. |
| 2013/0338448 A1 | 12/2013 | Libbus et al. |
| 2013/0338472 A1 | 12/2013 | Macia Barber et al. |
| 2014/0012154 A1 | 1/2014 | Mazar et al. |
| 2014/0140359 A1 | 5/2014 | Kalevo et al. |
| 2014/0189928 A1 | 7/2014 | Oleson et al. |
| 2014/0206977 A1 | 7/2014 | Bahney et al. |
| 2014/0215246 A1 | 7/2014 | Lee et al. |
| 2014/0358193 A1 | 12/2014 | Lyons et al. |
| 2015/0048836 A1 | 2/2015 | Guthrie et al. |
| 2015/0065842 A1 | 3/2015 | Lee et al. |
| 2015/0165211 A1 | 6/2015 | Naqvi et al. |
| 2015/0177175 A1 | 6/2015 | Elder et al. |
| 2015/0257670 A1 | 9/2015 | Ortega et al. |
| 2015/0359489 A1* | 12/2015 | Baudenbacher .... G06F 19/3418 600/300 |
| 2016/0217691 A1 | 7/2016 | Kadobayashi et al. |

FOREIGN PATENT DOCUMENTS

| | | | |
|---|---|---|---|
| EP | 2438851 | 4/2012 | |
| EP | 2438852 | 4/2012 | |
| EP | 2465415 | 6/2012 | |
| EP | 2589333 | 5/2013 | |
| JP | H06319711 | 11/1994 | |
| JP | 2004129788 | 4/2004 | |
| WO | 0078213 | 12/2000 | |
| WO | 03032192 | 4/2003 | |
| WO | 2006009767 | 1/2006 | |
| WO | 2006014806 | 2/2006 | |
| WO | WO 2007066270 A2 * | 6/2007 | ......... A61B 5/04085 |
| WO | 2007092543 | 8/2007 | |
| WO | 2008010216 | 1/2008 | |
| WO | 2008057884 | 5/2008 | |
| WO | 2009036306 | 3/2009 | |
| WO | 2009036313 | 3/2009 | |
| WO | 2009036327 | 3/2009 | |
| WO | 2009112976 | 9/2009 | |
| WO | 2009112978 | 9/2009 | |
| WO | 2009112979 | 9/2009 | |
| WO | 2009142975 | 11/2009 | |
| WO | 2010066507 | 6/2010 | |
| WO | 2010105045 | 9/2010 | |
| WO | 2011047207 | 4/2011 | |
| WO | 2012140559 | 10/2012 | |
| WO | 2012146957 | 11/2012 | |

OTHER PUBLICATIONS

Duttweiler et al., "Probability Estimation in Arithmetic and Adaptive-Huffman Entropy Coders," IEEE Transactions on Image Processing. vol. 4, No. 3, Mar. 1, 1995, pp. 237-246.

Gupta et al., "An ECG Compression Technique for Telecardiology Application," India Conference (INDICON), 2011 Annual IEEE, Dec. 16, 2011, pp. 1-4.

Nave et al., "ECG Compression Using Long-Term Prediction," IEEE Transactions on Biomedical Engineering, IEEE Service Center, NY, USA, vol. 40, No. 9, Sep. 1, 1993, pp. 877-885.

Skretting et al., "Improved Huffman Coding Using Recursive Splitting," NORSIG, Jan. 1, 1999.

(56) References Cited

OTHER PUBLICATIONS 15 of the Hottest Wearable Gadgets, URL <http://thehottestgadgets.com/2008/09/the-15-hottest-wearable-gadgets-001253> (Web page cached on Sep. 27, 2008).
Alivecor's Heart Monitor for iPhone Receives FDA Clearance, URL <http://www.businesswire.com/news/home/20121203005545/en/AliveCor%E2%80%99s-Heart-Monitor-iPhone-Receives-FDA-Clearance#.U7rtq7FVTyF> (Dec. 3, 2012).
Bharadwaj et al., Techniques for Accurate ECG signal processing, EE Times, URL <www.eetimes.com/document.asp?doc_id=1278571> (Feb. 14, 2011).
Chen et al., "Monitoring Body Temperature of Newborn Infants At Neonatal Intensive Care Units Using Wearable Sensors," BodyNets 2010, Corfu Island, Greece. (Sep. 10, 2010).
Epstein, Andrew E. et al.; ACC/AHA/HRS 2008 Guidelines for Device-Based Therapy of Cardiac Rhythm Abnormalities. J. Am. Coll. Cardiol. 2008; 51; eI-e62, 66 Pgs.
Fitbit automatically tracks your fitness and sleep, URL <http://www.fitbit.com/> (Web page cached on Sep. 10, 2008).
Smith, Kevin, "Jawbone Up Vs. Fitbit Flex: Which Is the Best Fitness Band?" URL <http://www.businessinsider.com/fitbit-flex-vs-jawbone-up-2013-5?op=1> (Jun. 1, 2013).
Kligfield, Paul et al., Recommendations for the Standardization and Interpretation of the Electrocardiogram: Part I. J.Am.Coll. Cardiol; 2007; 49; 1109-27, 75 Pgs.
Lauren Gravitz, "When Your Diet Needs a Band-Aid," Technology Review, MIT. (May 1, 2009).
Lieberman, Jonathan, "How Telemedicine Is Aiding Prompt ECG Diagnosis in Primary Care," British Journal of Community Nursing, vol. 13, No. 3, Mar. 1, 2008 (Mar. 1, 2008), pp. 123-126, XP009155082, ISSN: 1462-4753.
McManus et al., "A Novel Application for the Detection of an Irregular Pulse using an iPhone 4S in Patients with Atrial Fibrillation," vol. 10(3), pp. 315-319 (Mar. 2013).
Nike+ Fuel Band, URL <http://www.nike.com/us/en_us/c/nikeplus-fuelband> (Web page cached on Jan. 11, 2013).
P. Libby et al.,"Braunwald's Heart Disease—ATextbook of Cardiovascular Medicine," Chs. 11, pp. 125-148 and 12, pp. 149-193 (8th ed. 2008), American Heart Association.
Initial hands-on with Polar Loop activity tracker, URL <http://www.dcrainmaker.com/2013/09/polar-loop-firstlook.html> (Sep. 17, 2013).
Sittig et al., "A Computer-Based Outpatient Clinical Referral System," International Journal of Medical Informatics, Shannon, IR, vol. 55, No. 2, Aug. 1, 1999, pp. 149-158, XO004262434, ISSN: 1386-5056(99)00027-1.
Sleepview, URL <http://www.clevemed.com/sleepview/overview.shtml> (Web pages cached on Feb. 23, 2010, Dec. 29, 2012 and Sep. 4, 2013).
Actigraphy/ Circadian Rhythm SOMNOwatch, URL <http://www.somnomedics.eu/news-events/publications/somnowatchtm.html> (Web page cached on Jan. 23, 2010).
Zio Event Card, URL <http://www.irhythmtech.com/zio-solution/zio-event/> (Web page cached on Mar. 11, 2013).
Zio Patch System, URL <http://www.irhythmtech.com/zio-solution/zio-system/index.html> (Web page cached on Sep. 8, 2013).
Seifert, Dan, "Samsung dives into fitness wearable with the Gear Fit/ The Verge," URL <http://www.theverge.com/2014/2/24/5440310/samsung-dives-into-fitness-wearables-with-the-gear-fit> (Feb. 24, 2014).
Soper, Taylor, "Samsung's new Galaxy S5 flagship phone has fingerprint reader, heart rate monitor," URL <http://www.geekwire.com/2014/samsung-galaxy-s5-fingerprint> (Feb. 24, 2014).
Dolcourt, Jessica, "See the Samsung Galaxy S5's Heart rate monitor in action," URL <http://www.cnet.com/news/see-the-samsung-galaxy-s5s-heart-rate-monitor-in-action> (Feb. 25, 2014).
Saadi et al. "Heart Rhythm Analysis Using ECG Recorded With a Novel Sternum Based Patch Technology—A Pilot Study." Cardio technix 2013—Proceedings of the International Congress on Cardiovascular Technologies, Sep. 20, 2013.
Anonymous. "Omegawave Launches Consumer App 2.0 in U.S. Endurance Sportswire—Endurance Sportswire." Jul. 11, 2013. URL:http://endurancesportswire.com/omegawave-launches-consumer-app-2-0-in-u-s/.
Chan et al. "Wireless Patch Sensor for Remote Monitoring of Heart Rate, Respiration, Activity, and Falls." pp. 6115-6118. 2013 35th Annual International Conference of the IEEE Engineering in Medical and Biology Society. Jul. 1, 2013.
Wei et al. "A Stretchable and Flexible System for Skin-Mounted Measurement of Motion Tracking and Physiological Signals." pp. 5772-5775. 2014 36th Annual International Conference of the IEEE Engineering in Medicine and Biology Society. Aug. 26, 2014.
Daoud et al. "Fall Detection Using Shimmer Technology and Multiresolution Analysis." Aug. 2, 2013. URL: https://decibel.ni.com/content/docs/DOC-26652.
Libbus. "Adherent Cardiac Monitor With Wireless Fall Detection for Patients With Unexplained Syncope." Abstracts of the First AMA—IEEE Medical Technology Conference on Individualized Healthcare. May 22, 2010.
A Voss et al., "Linear and Nonlinear Methods for Analyses of Cardiovascular Variability in Bipolar Disorders," Bipolar Disorders, votl. 8, No. 5p1, Oct. 1, 2006, pp. 441-452, XP55273826, DK ISSN: 1398-5647, DOI: 10.1111/.1399-5618.2006.00364.x.
"Varicrad-Kardi Software User's Manual Rev. 1.1", Jul. 8, 2009 (Jul. 8, 2009), XP002757888, retrieved from the Internet: URL:http://www.ehrlich.tv/KARDiVAR-Software.pdf [retrieved on May 20, 2016].
"Vedapulse UK," Jan. 1, 2014 (Jan. 1, 2014), XP002757887, Retrieved from the Internet: URL:http://www.vedapulseuk.com/diagnostic/ [retrieved on May 19, 2016].
Health Research—Hexoskin Biometric Shirt | Hexoskin URL:http://www.hexoskin.com/pages/health-research (Web page cached on Dec. 2, 2014).
Jacob Kastrenakes, "Apple Watch uses four sensors to detect your pulse," Sep. 9, 2014. URL: http://www.theverge.com/2014/9/9/6126991/apple-watch-four-back-sensors-detect-activity.
Nicole Lee, "Samsung Gear S review: an ambitious and painfully flawed smartwatch," Dec. 1, 2014. URL:http://www.engadget.com/2014/12/01/samsung-gear-s-review/.

\* cited by examiner

Fig. 13. (Con'd)
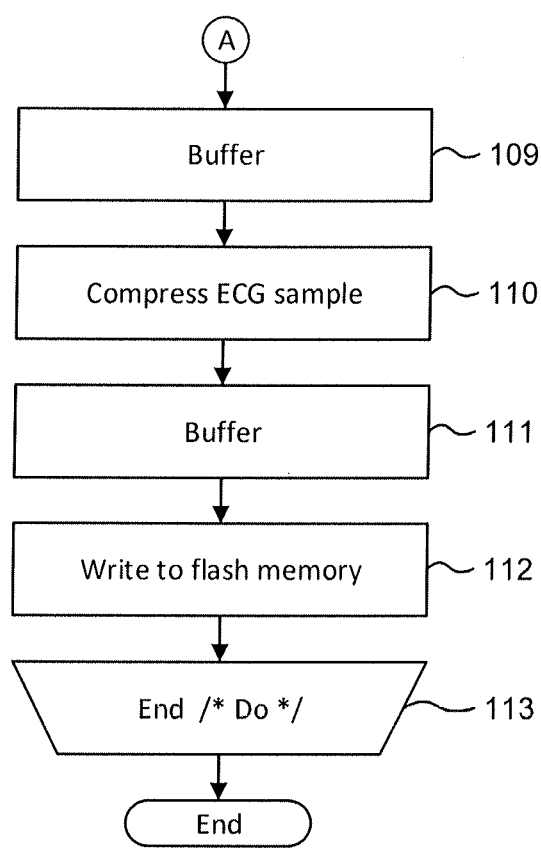

160

180

210

AMBULATORY EXTENDED-WEAR ELECTROCARDIOGRAPHY AND SYNCOPE SENSOR MONITOR

CROSS-REFERENCE TO RELATED APPLICATION

This non-provisional patent application is a continuation-in-part of U.S. patent application Ser. No. 14/082,108, filed Nov. 16, 2013, pending, which is a continuation-in-part of U.S. patent application Ser. No. 14/080,717, filed Nov. 14, 2013, pending, and a continuation-in-part of U.S. patent application Ser. No. 14/080,725, filed Nov. 14, 2013, pending, which further claims priority under 35 U.S.C. §119(e) to U.S. Provisional Patent application, Ser. No. 61/882,403, filed Sep. 25, 2013, the disclosures of which are incorporated by reference; this non-provisional patent application is also a continuation-in-part of U.S. patent application Ser. No. 14/488,230, filed Sep. 16, 2014, pending, which is a continuation-in-part of U.S. patent application Ser. No. 14/080,725, filed Nov. 14, 2013, pending, and further claims priority under 35 U.S.C. §119(e) to U.S. Provisional Patent application, Ser. No. 61/882,403, filed Sep. 25, 2013, the disclosures of which are incorporated by reference.

FIELD

This application relates in general to physiological monitoring and, in particular, to an ambulatory, extended-wear electrocardiography and syncope sensor monitor.

BACKGROUND

An ECG measures the electrical signals emitted by the heart, which are generated by propagation of action potentials that trigger depolarization of heart fibers. Physiologically, transmembrane ionic currents are generated within the heart during cardiac electrical signals from well-established, traditional chest locations. Cardiac depolarization originates high in the right atrium in the sinoatrial (SA) node before spreading leftward towards the left atrium and inferiorly towards the atrioventricular (AV) node. After a delay occasioned by the AV node, the depolarization impulse transits the Bundle of His and moves into the right and left bundle branches as well as Purkinje fibers to activate the right and left ventricles.

During each cardiac cycle, the ionic currents create an electrical field in and around the heart, which can be detected by ECG electrodes placed on the skin over the anterior thoracic region of the patient's body to the lower right and to the lower left of the sternum on the left anterior chest and on the limbs. Cardiac electrical activity is then visually represented in an ECG trace by PQRSTU-waveforms, which can be interpreted post-ECG recordation to derive heart rate and physiology. The P-wave represents atrial electrical activity, and the QRSTU components represent ventricular electrical activity. Specifically, a P-wave represents atrial depolarization, which causes atrial contraction.

P-wave analysis based on ECG monitoring is critical to accurate cardiac rhythm diagnosis and focuses on localizing the sites of origin and pathways underlying arrhythmic conditions. Certain arrhythmias can cause a clinical problem referred to as syncope. Syncope, or a transient loss of consciousness with spontaneous recovery, is often caused by a dramatic drop in blood pressure that leads to a loss of consciousness due to cerebral hypofusion. Conditions that produce cardiac-based syncope are often serious, may be harbingers of sudden death, and can require serious therapy. Such conditions include high-grade AV block, which can lead to an abrupt loss of consciousness and is diagnosed based on the relative position and temporal association of the P-wave with the QRS-wave. Transient ventricular tachycardia is another such condition that can result in syncope where there is a rapid ventricular response (with a series of rapid QRS signals) that is disassociated from atrial activity or the P-wave. However, not all episodes of high-grade AV block or ventricular tachycardia result in syncope; some superficially similar arrhythmias are better tolerated than other arrhythmias, even in the same patient. Often to know from the specific type of arrhythmia alone whether or not syncope will occur is not possible.

Cardiac rhythm disorders are often sporadic and may not occur in-clinic during a conventional 12-second ECG. Syncope episodes can be especially sporadic and infrequent; further, these episodes are problematic because they are common, costly, often disabling, may cause injury, and may be the only warning sign prior to sudden cardiac death (SCD). Establishing the underlying cause of these episodes is important because the cause greatly influences the treatment and prognosis. Cardiac-based syncope portends the highest mortality, in contrast to neurally mediated syncope, such as vasodepressor syncope, or where the patient presents with an apparent syncope episode that is not true syncope, but is due to an alternative physiological condition, including metabolic conditions, such as hypoglycemia; neurological causes, such as seizures; and psychiatric disorders. Moreover, syncope can arise slowly or abruptly. A patient who is gradually aware that he or she may lose consciousness is less prone to injury. However, an abrupt loss of consciousness is much more dangerous because a person with abrupt syncope may be standing and fall suddenly, leading to injury. Therefore, knowing whether or not a condition will likely cause a fall is valuable in properly managing patients, regardless of the basis.

The diagnosis, prognosis, and treatment of syncope can be improved through concomitant recording of syncope episodes as well as ECG data. Where syncope episodes are based on a cardiac condition, diagnosis and treatment are especially important due to the higher mortality rate correlated with cardiac-based syncope episodes. Moreover, both cardiac-based and neurally mediated syncope episodes may require a different treatments. For cardiac arrhythmia-induced syncope, a pace-maker might be helpful, whereas for neurally mediated syncope, a specific drug therapy may be helpful. Correlating motor activity and cardiovascular ECG data is important for improving diagnostic specificity as well as guiding therapy. Moreover, such combined sensor technology can optimize and improve monitoring recommendations during recovery or rehabilitation programs.

Further, combining an ECG recorder with a syncope detection mechanism that detects a sudden collapse is especially valuable because the combination can aid in including (or excluding) a basis for cardiac arrhythmia and inform the doctor on the seriousness of a condition where the recorder can identify falls due to arrhythmia. Continuous ECG monitoring with P-wave-centric action potential acquisition over an extended time period is more likely to elucidate sporadic cardiac events that can be specifically identified and diagnosed, including cardiac events that produce syncope. A longer monitoring period enhances the likelihood of diagnosing an episodic arrhythmia responsible for an episodic syncope episode. However, recording sufficient ECG and physiological data continuously over an extended time period to both diagnose an arrhythmia and syncope that produces a fall remains a technical challenge on multiple levels: cost, comfort, reliability, and both rhythm as well as fall accuracy.

An example of this technical challenge can be seen with actigraphy sensors, such as accelerometers, which can be used to detect movements that occur during syncope episodes, such as falls and sudden postural changes that a patient may experience during a syncope episode while sitting down. Different kinds of actigraphs exist. For example, sleep actigraphs are typically worn similar to a watch on the wrist of the non-dominant arm and can be worn for weeks. Activity actigraphs are worn and used similar to a pedometer, around the waist and near the hip; they are useful in determining the level of activity as well as, potentially, calories and can be worn for a number of days. Movement actigraphs are typically larger and are worn on the shoulder of the dominant arm. Further, movement actigraphs include 3-D actigraphs, which are distinct from 1-D actigraphs that are used during sleep as well as activity actigraphy and tend to include a high sample rate as well as large memory; thus, they are often only used for a few hours. However, wearing two separate devices, one for ECG and another for collecting actigraphy to detect syncope episodes, creates problems. For example, recordings from two separate devices are not synchronized, which could result in temporally mismatched movements indicative of syncope and ECG data.

Current combined actigraphy and ECG monitors are similarly lacking in meeting the technical challenge. For example, U.S. Pat. No. 8,460,189, to Libbus et al. ("Libbus") discloses an adherent wearable cardiac monitor that includes at least two measurement electrodes and an accelerometer. The device includes a reusable electronics module and a disposable adherent patch, which includes the electrodes. ECG monitoring can be conducted using multiple disposable patches adhered to different locations on the patient's body. The device includes a processor configured to control data collection and transmission from the ECG circuitry, including generating and processing ECG signals as well as data acquired from two or more electrodes. The ECG circuitry and electrodes can be coupled in multiple ways to define an ECG vector; further, the ECG vector orientation can be determined in response to the measuring electrodes' polarity and the orientation of the electrode measurement axis. The accelerometer can be used to determine the orientation of the measuring electrodes at each location. The ECG signals measured at different locations can be rotated based on the accelerometer data to modify the amplitude and direction of the ECG features to approximate a standard ECG vector. The signals recorded at different locations can be combined by summing a scaled version of each signal. Libbus further discloses that inner ECG electrodes may be positioned near outer electrodes to increase the voltage of the measured ECG signals. However, Libbus treats ECG signal acquisition as measuring a simple aggregate directional data signal without differentiating between the distinct types of cardiac electrical activities presented by an ECG waveform, particularly atrial (P-wave) activity. Further, Libbus does not address using the accelerometer data to identify movements that could be indicative of syncope.

Similarly lacking is the SOMNOwatch™ manufactured by SOMNOmedics, a wearable watch-shaped monitoring device that records sleep actigraphy, recognizes sleep/wake rhythms, records activity actigraphs, aids attention deficit and hyperactivity disorder (ADHD) diagnosis, reads ECGs, and records heart rate. The SOMNOwatch™ can only store raw data from a single channel ECG for up to 18 hours, requires a software system that synchronizes heart rate with motor activity, and does not record specific movements, limiting the usefulness of the device for detecting syncope episodes through recognition of movements indicative of syncope, such as falls and sudden postural changes.

Therefore, a need remains for a low-cost, extended-wear, continuously recording ECG monitor coupled with a syncope sensor attuned to detecting low-amplitude cardiac action potential propagation for arrhythmia diagnosis, particularly through atrial activation P-waves, that is practicably feasible for long-term wear and correlating cardiovascular events with movements indicative of syncope or a loss of consciousness.

SUMMARY

ECG and syncope monitoring can be provided through a lightweight wearable monitor that permits detection of syncope events, events indicative of syncope episodes, and collecting ECG data contemporaneous to the events. The monitor includes two components, a flexible extended wear electrode patch and a reusable monitor recorder that removably snaps into a receptacle on the electrode patch and includes a syncope detector. The wearable monitor sits centrally (in the midline) on the patient's chest along the sternum oriented top-to-bottom. The ECG electrodes on the electrode patch are tailored to be positioned axially along the midline of the sternum for capturing action potential propagation in an orientation that corresponds to the aVF lead used in a conventional 12-lead ECG that is used to sense positive or upright P-waves. The placement of the wearable monitor in a location at the sternal midline (or immediately to either side of the sternum), with its unique, narrow hourglass shape, significantly improves the ability of the wearable monitor to cutaneously sense cardiac electrical potential signals, particularly the P-wave (or atrial activity) and, to a lesser extent, the QRS interval signals indicating ventricular activity in the ECG waveforms. The monitor includes a syncope sensor capable of detecting the syncope events. The syncope sensor can include an actigraphy sensors that can movements indicative of syncope, such as falls and sudden posture changes. The syncope sensor can also include a patient-mediated tactile feedback syncope button, which the patient can press to indicate an onset of a syncope episode.

Moreover, the electrocardiography monitor offers superior patient comfort, convenience and user-friendliness. The electrode patch is specifically designed for ease of use by a patient (or caregiver); assistance by professional medical personnel is not required. The patient is free to replace the electrode patch at any time and need not wait for a doctor's appointment to have a new electrode patch placed. Patients can easily be taught to find the familiar physical landmarks on the body necessary for proper placement of the electrode patch. Doing so is nearly intuitive and within the grasp of most any person of nearly any age and ability. Empowering patients with the knowledge to place the electrode patch in the right place ensures that the ECG electrodes will be correctly positioned on the skin, no matter the number of times that the electrode patch is replaced. In addition, the monitor recorder operates automatically, and the patient only need snap the monitor recorder into place on the electrode patch to initiate ECG monitoring. Thus, the synergistic combination of the electrode patch and monitor recorder makes the use of the electrocardiography monitor in a reliable and virtually foolproof way to monitor a patient's ECG and physiology for an extended, or even open-ended, period of time. Moreover, ECG monitoring through this combination concomitant with monitoring for syncope episodes extends the duration for detection and, thus, the ability of patients and physicians determine the causes underlying syncope, which can be difficult because syncope episodes are often sporadic and infrequent.

One embodiment provides an ambulatory, extended-wear electrocardiography and syncope sensor monitor recorder, which includes a sealed housing adapted to be removably secured into a non-conductive receptacle on a disposable extended wear electrode patch. Further, the recorder includes electronic circuitry within the sealed housing, which includes an externally-powered, low-power microcontroller that is operable to execute under microprogrammable control as specified in a firmware. The electronic circuitry further includes an electrocardiographic front end circuit electrically interfaced to the microcontroller and operable to sense electrocardiographic signals through electrocardiographic electrodes that are provided on the disposable extended wear electrode patch. Each of the electrocardiographic electrodes is adapted to be positioned axially along the midline of the sternum to capture action potential propagation. In addition, the circuitry includes a syncope sensor that is electrically interfaced with the microcontroller and operable to sense syncope events, which are events that are indicative of a syncope episode. Finally, the recorder includes an externally-powered flash memory electrically that is interfaced with the microcontroller and operable to store samples of the electrocardiographic signals and sensed syncope data.

A further embodiment provides an ambulatory, extended-wear electrocardiography and syncope sensor monitor optimized for capturing low amplitude cardiac action potential propagation, which includes a disposable extended wear electrode patch. The patch is composed of a flexible backing that is formed from an elongated strip of stretchable material with a narrow longitudinal midsection and, on each end, a contact surface at least partially coated with an adhesive dressing provided as a crimp relief. The patch also includes a pair of electrocardiographic electrodes that are conductively exposed on the contact surface at each end of the elongated strip; a non-conductive receptacle that is adhered to an outward-facing end of the elongated strip and comprising a plurality of electrical pads; and a flexible circuit that is affixed on each end of the elongated strip for strain relief and that includes a pair of circuit traces, which are electrically coupled to the pair of electrocardiographic electrodes and a pair of the electrical pads. The monitor further includes a sealed housing adapted to be removably secured into a non-conductive receptacle on a disposable extended wear electrode patch and an electronic circuitry within the sealed housing. The sealed housing includes an externally-powered, low-power microcontroller that is operable to execute under microprogrammable control as specified in a firmware. The housing also includes an electrocardiographic front end circuit that is electrically interfaced to the microcontroller and operable to sense electrocardiographic signals through electrocardiographic electrodes, which are provided on the disposable extended wear electrode patch. Each of the electrocardiographic electrodes is adapted to be positioned axially along the midline of the sternum to capture action potential propagation. Finally, the monitor includes a syncope sensor, which is electrically interfaced with the microcontroller and operable to sense syncope events, as well as an externally-powered flash memory, which is electrically interfaced with the microcontroller and operable to store samples of the electrocardiographic signals and sensed syncope data.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

DETAILED DESCRIPTION

Figure 1:
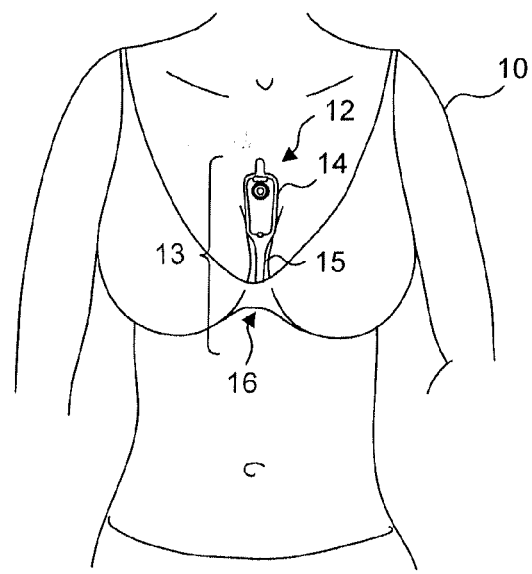
FIGS. 1 and 2 are diagrams showing, by way of examples, an ambulatory, extended-wear electrocardiography and syncope sensor monitor recorder, including an extended wear electrode patch, in accordance with one embodiment, respectively fitted to the sternal region of a female patient and a male patient.
Figure 2:
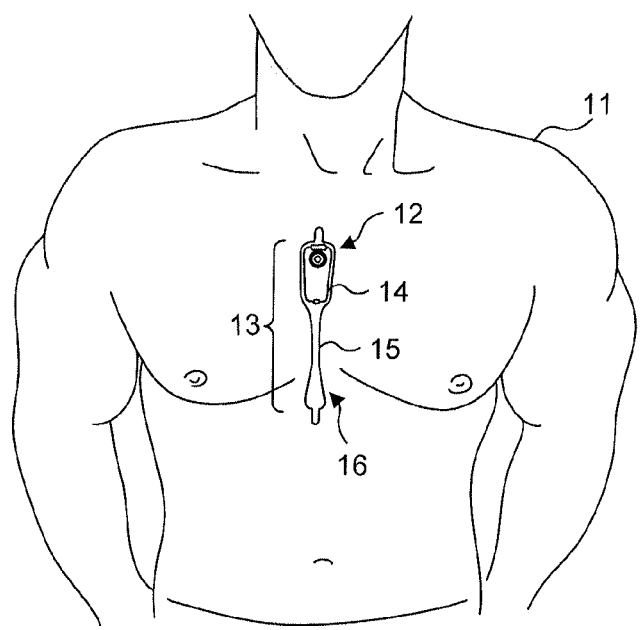

ECG, syncope, and other physiological monitoring can be provided through an extended-wear ambulatory monitor that includes two components, a flexible extended wear electrode patch and a removable reusable (or single use) monitor recorder. Both the electrode patch and the monitor recorder are optimized to monitor syncope events and collecting ECG data, capturing electrical signals from the propagation of low-amplitude, relatively low-frequency content cardiac action potentials, particularly the P-waves generated during atrial activation, as described in the commonly-assigned U.S. patent application, entitled "Ambulatory electrocardiography monitoring patch optimized for capturing low amplitude cardiac action potential propagation," Ser. No. 14/488,230, filed Sep. 16, 2014, pending, the disclosure of which is incorporated by reference. Syncope events are events that are indicative of a syncope episode and can be detecting using a sensor in the monitor that recognizes movements associated with a syncope episode, such as a fall or a sudden postural change, as further described below. Further, the monitor is configured to receive patient feedback indicating an onset of a syncope episode, allowing to detect syncope events even in the absence of movements characteristic of syncope, as further described below. FIGS. 1 and 2 are diagrams showing, by way of example, an ambulatory extended-wear electrocardiography and syncope monitor 12 ("wearable monitor 12"), including a monitor recorder 14, in accordance with one embodiment, respectively fitted to the sternal region of a female patient 10 and a male patient 11. The wearable monitor 12 sits centrally positioned axially along the sternal midline 16 on the patient's chest along the sternum 13 and oriented top-to-bottom with the monitor recorder 14 preferably situated towards the patient's head. In a further embodiment, the orientation of the wearable monitor 12 can be corrected post-monitoring, as further described infra, for instance, if the wearable monitor 12 is inadvertently fitted upside down.

The electrode patch 15 is shaped to fit comfortably and conform to the contours of the patient's chest approximately centered on the sternal midline 16 (or immediately to either side of the sternum 13). The distal end of the electrode patch 15, under which a lower or inferior pole (ECG electrode) is adhered, extends towards the Xiphoid process and lower sternum and, depending upon the patient's build, may straddle the region over the Xiphoid process and lower sternum. The proximal end of the electrode patch 15, located under the monitor recorder 14, under which an upper or superior pole (ECG electrode) is adhered, is below the manubrium and, depending upon patient's build, may straddle the region over the manubrium.

During ECG monitoring, the amplitude and strength of action potentials sensed on the body's surface are affected to varying degrees by cardiac, cellular, extracellular, vector of current flow, and physical factors, such as obesity, dermatitis, large breasts, and high-impedance skin, as can occur in dark-skinned individuals. Sensing along the sternal midline 16 (or immediately to either side of the sternum 13) significantly improves the ability of the wearable monitor 12 to cutaneously sense cardiac electric signals, particularly P-waves (or atrial activity) and, to a lesser extent, QRS interval signals in ECG waveforms that indicate ventricular activity by countering some of the effects from these factors.

Figure 3:
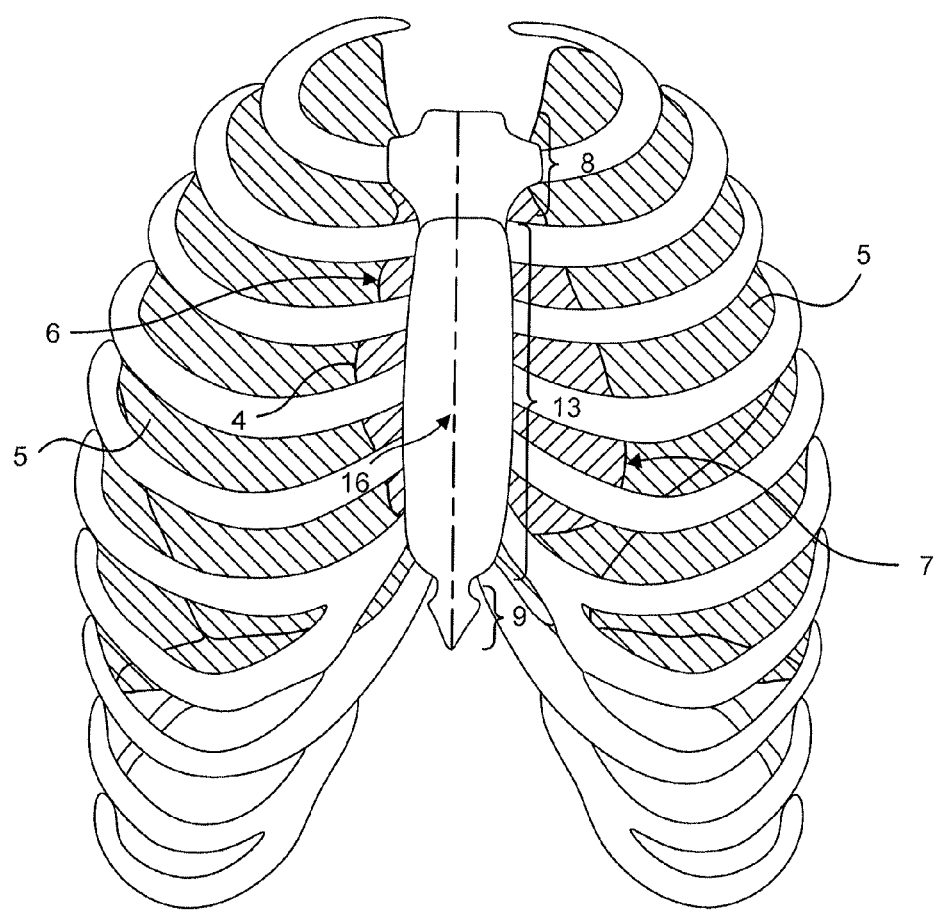
FIG. 3 is a front anatomical view showing, by way of illustration, the locations of the heart and lungs within the rib cage of an adult human.

The ability to sense low-amplitude, low-frequency content body surface potentials is directly related to the location of ECG electrodes on the skin's surface and the ability of the sensing circuitry to capture these electrical signals. FIG. 3 is a front anatomical view showing, by way of illustration, the locations of the heart 4 and lungs 5 within an adult human rib cage. Depending on the location of an ECG electrode on the chest, the ECG electrode may be separated from activation regions within the heart 4 by differing combinations of internal tissues and body structures, including heart muscle, intracardiac blood, the pericardium, intrathoracic blood and fluids, the lungs 5, skeletal muscle, bone structure, subcutaneous fat, and the skin as well as any contaminants present between the skin's surface and electrode signal detection. The degree of amplitude degradation for cardiac transmembrane potentials increases with the number of tissue boundaries encountered between the heart 4 and the skin's surface. The cardiac electrical field is degraded each time the transmembrane potentials encounter a physical boundary separating adjoining tissues due to differences in the respective tissues' electrical resistances. In addition, other non-spatial factors, such as pericardial effusion, emphysema, or fluid accumulation in the lungs, as further explained infra, can further degrade body surface potentials.

Internal tissues and body structures can adversely affect the current strength and signal fidelity of all body surface potentials; however, low-amplitude cardiac action potentials, particularly P-waves with a normative amplitude of less than 0.25 microvolts (mV) and a normative duration of less than 120 milliseconds (ms), are most apt to be negatively impacted. The atria 6 are generally located posteriorly within the thoracic cavity (except for the anterior right atrium and right atrial appendage), and, physically, the left atrium is the portion of the heart 4 furthest away from the surface of the skin on the chest. Conversely, ventricles 7, which generate larger amplitude signals, are generally located anteriorly with the anterior right ventricle and most of the left ventricle situated relatively close to the skin surface on the chest, which contributes to the relatively stronger ventricular waveform amplitudes. Thus, the quality of P-waves (and other amplitude action potential signals that are already low) is more susceptible to weakening from intervening tissues and structures than the waveforms associated with ventricular activation.

The importance of positioning ECG electrodes along the sternal midline 15 has largely been overlooked by conventional approaches to ECG monitoring, in part due to the inability of their sensing circuitry to reliably detect low-amplitude, low-frequency content electrical signals, particularly P-waves. In turn, the inability to keenly sense P-waves has motivated ECG electrode placement in other non-sternal midline thoracic locations, where the QRSTU components that represent ventricular electrical activity are more readily detectable by their sensing circuitry than P-waves. In addition, ECG electrode placement along the sternal midline 15 presents major patient wearability challenges, such as fitting a monitoring ensemble within the narrow confines of the inter-mammary cleft between the breasts, that, to a large extent, drive physical packaging concerns, which can be incompatible with ECG monitors intended for placement, for example, in the upper pectoral region or other non-sternal midline thoracic location. In contrast, the wearable monitor 12 uses an electrode patch 15 specifically intended for extended wear placement in a location at the sternal midline 16 (or immediately to either side of the sternum 13). Combined with a monitor recorder 14 that uses sensing circuitry optimized to preserve the characteristics of low-amplitude cardiac action potentials, especially signals from the atria, as further described infra with reference to FIG. 12, the electrode patch 15 helps to significantly improve atrial activation (P-wave) sensing through placement in a body location that robustly minimizes the effects of tissue and body structure.

Referring back to FIGS. 1 and 2, placement of the wearable monitor 12 in the sternal midline 13 region positions the electrode patch 15 ECG electrodes in locations better adapted to sensing and recording low-amplitude cardiac action potentials during atrial propagation (P-wave signals) than placement in other locations, such as the upper left pectoral region, which is common in most conventional ambulatory ECG monitors. The sternum 13 overlies the right atrium of the heart 4. As a result, action potential signals must travel through fewer layers of tissue and structure to reach the ECG electrodes of the electrode patch 15 on the body's surface along the sternal midline 13 compared with other monitoring locations, a distinction that is critically important to capturing low-frequency content electrical signals, such as P-waves.

Moreover, cardiac action potential propagation travels simultaneously along a north-to-south and right-to-left vector, beginning high in the right atrium and ultimately ending in the posterior and lateral region of the left ventricle. Cardiac depolarization originates high in the right atrium in the SA node before concurrently spreading leftward towards the left atrium and inferiorly towards the AV node. The ECG electrodes of the electrode patch 15 are placed with the upper or superior pole (ECG electrode) along the sternal midline 13 in the region of the manubrium and the lower or inferior pole (ECG electrode) along the sternal midline 13 in the region of the Xiphoid process 9 and lower sternum. The ECG electrodes are placed primarily in a north-to-south orientation along the sternum 13 that corresponds to the north-to-south waveform vector exhibited during atrial activation. This orientation corresponds to the aVF lead used in a conventional 12-lead ECG that is used to sense positive or upright P-waves.

Furthermore, the thoracic region underlying the sternum 13 along the midline 16 between the manubrium 8 and Xiphoid process 9 is relatively free of lung tissue, musculature, and other internal body structures that could occlude the electrical signal path between the heart 4, particularly the atria, and ECG electrodes placed on the surface of the skin. Fewer obstructions means that cardiac electrical potentials encounter fewer boundaries between different tissues. As a result, compared with other thoracic ECG sensing locations, the cardiac electrical field is less altered when sensed dermally along the sternal midline 13. Further, the proximity of the sternal midline 16 to the ventricles 7 facilitates sensing of right ventricular activity and provides superior recordation of the QRS interval, again, in part due to the relatively clear electrical path between the heart 4 and the skin surface.

Finally, non-spatial factors can affect transmembrane action potential shape and conductivity. For instance, myocardial ischemia, an acute cardiac condition, can cause a transient increase in blood perfusion in the lungs 5. The perfused blood can significantly increase electrical resistance across the lungs 5 and, therefore, degrade transmission of the cardiac electrical field to the skin's surface. However, placement of the wearable monitor 12 along the sternal midline 16 in the inter-mammary cleft between the breasts is relatively resilient to the adverse cardiac action potential degradation effects caused by ischemic conditions because the body surface potentials from a location that is relatively clear of underlying lung tissue and fat help compensate for the loss of signal amplitude and content. Thus, the monitor recorder 14 can record the P-wave morphology that may be compromised by myocardial ischemia and, therefore, enhance the difficulty with diagnosing the specific arrhythmias that can be associated with myocardial ischemia.

Figure 4:
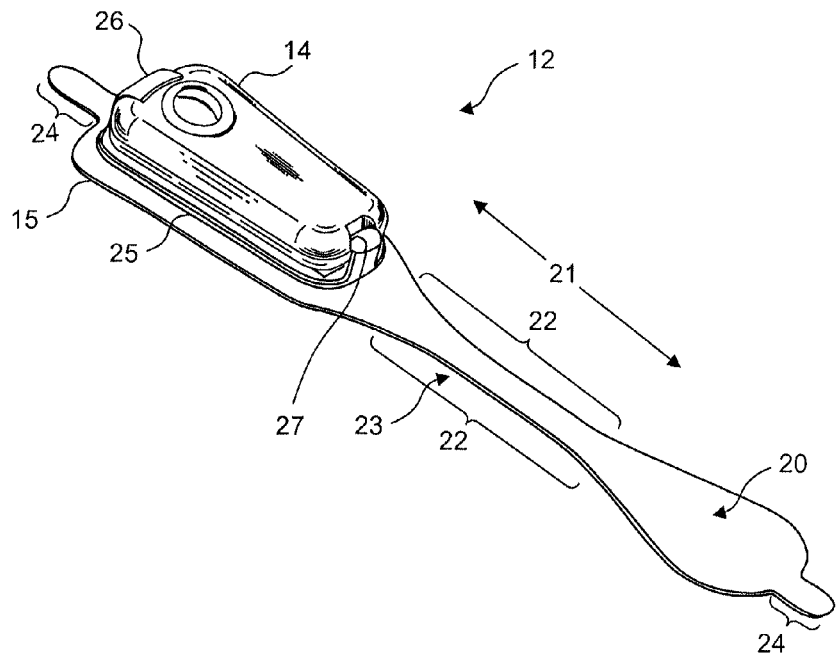
FIG. 4 is a perspective view showing an extended wear electrode patch in accordance with one embodiment with a monitor recorder inserted.

During use, the electrode patch 15 is first adhered to the skin along the sternal midline 16 (or immediately to either side of the sternum 13). A monitor recorder 14 is then snapped into place on the electrode patch 15 using an electromechanical docking interface to initiate ECG monitoring. FIG. 4 is a perspective view showing an extended wear electrode patch 15 in accordance with one embodiment where a monitor recorder 14 is inserted. The body of the electrode patch 15 is preferably constructed using a flexible backing 20 formed as an elongated strip 21 of wrap knit or similar stretchable material about 145 mm long and 32 mm at the widest point with a narrow longitudinal mid-section 23 evenly tapering inward from both sides. A pair of cut-outs 22 between the distal and proximal ends of the electrode patch 15 create a narrow longitudinal midsection 23 or "isthmus" and defines an elongated "hourglass"-like shape when viewed from above, such as described in commonly-assigned U.S. Design patent application, entitled "Extended Wear Electrode Patch," Ser. No. 29/472,045, filed Nov. 7, 2013, pending, the disclosure of which is incorporated by reference. The upper part of the "hourglass" is sized to allow an electrically non-conductive receptacle 25, which sits on top of the outward-facing surface of the electrode patch 15, to be affixed to the electrode patch 15 with an ECG electrode placed underneath on the patient-facing underside, or contact, surface of the electrode patch 15; the upper part of the "hourglass" has a longer and wider profile (but remains rounded and tapered to fit comfortably between the breasts) than the lower part of the "hourglass," which is sized primarily to allow just the placement of an ECG electrode of appropriate shape and surface area to record the P-wave and the QRS signals sufficiently given the inter-electrode spacing.

The electrode patch 15 incorporates features that significantly improve wearability, performance, and patient comfort throughout an extended monitoring period. The entire electrode patch 15 is lightweight in construction, which allows the patch to be resilient to disadhesing or falling off and, critically, to avoid creating distracting discomfort to the patient, even when the patient is asleep. In contrast, the weight of a heavy ECG monitor impedes patient mobility and will cause the monitor to constantly tug downwards and press on the patient's body, which can inflame the skin and lead to frequent adjustments by the patient to maintain comfort.

During every day wear, the electrode patch 15 is subjected to pushing, pulling, and torsional movements, including compressional and torsional forces when the patient bends forward as well as tensile and torsional forces when the patient leans backwards. To counter these stress forces, the electrode patch 15 incorporates crimp and strain reliefs, such as described in commonly-assigned U.S. patent application, entitled "Extended Wear Electrocardiography Patch," Ser. No. 14/080,717, filed Nov. 14, 2013, pending, the disclosure of which is incorporated by reference. In addition, the cut-outs 22 and longitudinal midsection 23 help minimize interference with and discomfort to breast tissue, particularly in women (and gynecomastic men). The cut-outs 22 and longitudinal midsection 23 further allow better conformity of the electrode patch 15 to sternal bowing and to the narrow isthmus of flat skin that can occur along the bottom of the inter-mammary cleft between the breasts, especially in buxom women. The cut-outs 22 and narrow and flexible longitudinal midsection 23 help the electrode patch 15 fit nicely between a pair of female breasts in the inter-mammary cleft. In one embodiment, the cut-outs 22 can be graduated to form the longitudinal midsection 23 as a narrow in-between stem or isthmus portion about 7 mm wide. In an additional embodiment, tabs 24 can respectively extend an additional 8 mm to 12 mm beyond the distal and proximal ends of the flexible backing 20 to facilitate adhering the electrode patch 15 to or removing the electrode patch 15 from the sternum 13. These tabs preferably lack adhesive on the underside, or contact, surface of the electrode patch 15. Still other shapes, cut-outs, and conformities to the electrode patch 15 are possible.

The monitor recorder 14 removably and re-usably snaps into an electrically non-conductive receptacle 25 during use. The monitor recorder 14 contains electronic circuitry for recording and storing the patient's electrocardiography as sensed via a pair of ECG electrodes provided on the electrode patch 15, as further described infra beginning with reference to FIG. 9. The non-conductive receptacle 25 is provided on the top surface of the flexible backing 20 with a retention catch 26 and tension clip 27 molded into the non-conductive receptacle 25 to conformably receive and securely hold the monitor recorder 14 in place.

Figure 5:
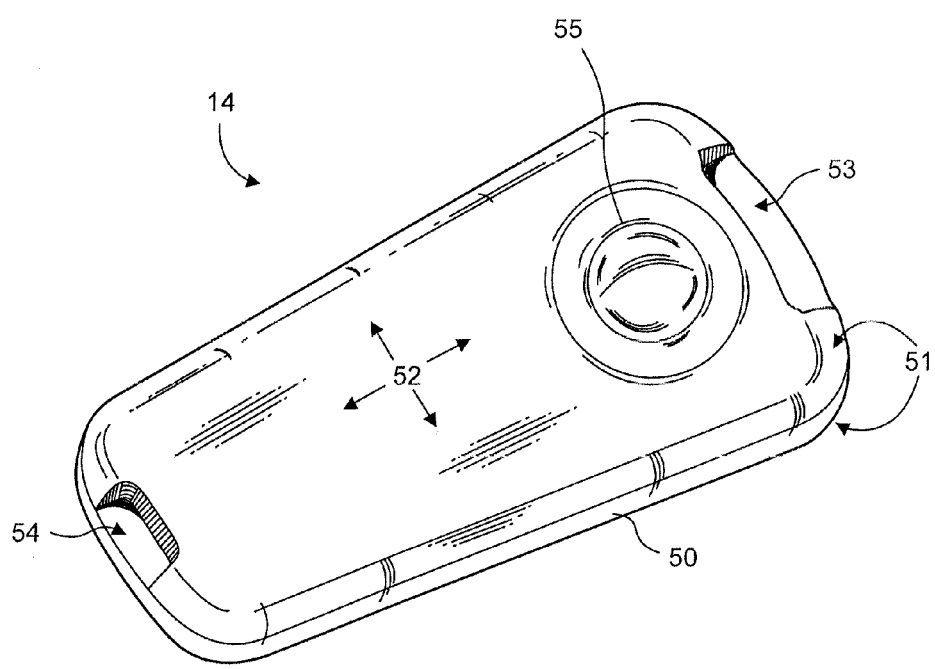
FIG. 5 is a perspective view showing the monitor recorder of FIG. 4.

The monitor recorder 14 includes a sealed housing that snaps into place in the non-conductive receptacle 25. FIG. 5 is a perspective view showing the monitor recorder 14 of FIG. 4. The sealed housing 50 of the monitor recorder 14 intentionally has a rounded isosceles trapezoidal-like shape 52 when viewed from above, such as described in commonly-assigned U.S. Design patent application, entitled "Electrocardiography Monitor," Ser. No. 29/472,046, filed Nov. 7, 2013, pending, the disclosure of which is incorporated by reference. The edges 51 along the top and bottom surfaces are rounded for patient comfort. The sealed housing 50 is approximately 47 mm long, 23 mm wide at the widest point, and 7 mm high, excluding a patient-operable tactile-feedback button 55. The sealed housing 50 can be molded out of polycarbonate, ABS, or an alloy of those two materials. The button 55 is waterproof and the button's top outer surface is molded silicon rubber or similar soft pliable material. A retention detent 53 and tension detent 54 are molded along the edges of the top surface of the housing 50 to, respectively, engage the retention catch 26 and the tension clip 27 molded into non-conductive receptacle 25. Other shapes, features, and conformities of the sealed housing 50 are possible.

The electrode patch 15 is intended to be disposable, while the monitor recorder 14 is designed for reuse and can be transferred to successive electrode patches 15 to ensure continuity of monitoring, if so desired. The monitor recorder 14 can be used only once, but single use effectively wastes the synergistic benefits provided by the combination of the disposable electrode patch and reusable monitor recorder, as further explained infra with reference to FIGS. 23A-C. The placement of the wearable monitor 12 in a location at the sternal midline 16 (or immediately to either side of the sternum 13) benefits long-term extended wear by removing the requirement that ECG electrodes be continually placed in the same spots on the skin throughout the monitoring period. Instead, the patient is free to place an electrode patch 15 anywhere within the general region of the sternum 13.

As a result, at any point during ECG monitoring, the patient's skin can recover from wearing electrode patch 15, which increases patient comfort and satisfaction, while the monitor recorder 14 ensures ECG monitoring continuity with minimal effort. A monitor recorder 14 is merely unsnapped from a worn out electrode patch 15, the worn out electrode patch 15 is removed from the skin, a new electrode patch 15 is adhered to the skin, possibly in a new spot immediately adjacent to the earlier location, and the same monitor recorder 14 is snapped into the new electrode patch 15 to re-initiate and continue the ECG monitoring.

Figure 6:
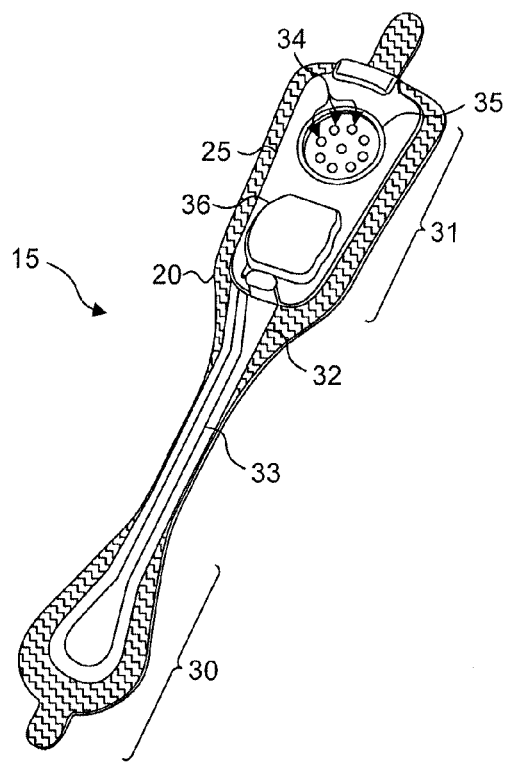
FIG. 6 is a perspective view showing the extended wear electrode patch of FIG. 4 without a monitor recorder inserted.

During use, the electrode patch 15 is first adhered to the skin in the sternal region. FIG. 6 is a perspective view showing the extended wear electrode patch 15 of FIG. 4 without a monitor recorder 14 inserted. A flexible circuit 32 is adhered to each end of the flexible backing 20. A distal circuit trace 33 from the distal end 30 of the flexible backing 20 and a proximal circuit trace (not shown) from the proximal end 31 of the flexible backing 20 electrically couple ECG electrodes (not shown) with a pair of electrical pads 34. In a further embodiment, the distal and proximal circuit traces are replaced with interlaced or sewn-in flexible wires, as further described infra beginning with reference to FIG. 19. The electrical pads 34 are provided within a moisture-resistant seal 35 formed on the bottom surface of the non-conductive receptacle 25. When the monitor recorder 14 is securely received into the non-conductive receptacle 25, that is, snapped into place, the electrical pads 34 interface to electrical contacts (not shown) protruding from the bottom surface of the monitor recorder 14. The moisture-resistant seal 35 enables the monitor recorder 14 to be worn at all times, even during showering or other activities that could expose the monitor recorder 14 to moisture or adverse conditions.

In addition, a battery compartment 36 is formed on the bottom surface of the non-conductive receptacle 25. A pair of battery leads (not shown) from the battery compartment 36 to another pair of the electrical pads 34 electrically interface the battery to the monitor recorder 14. The battery contained within the battery compartment 35 is a direct current (DC) power cell and can be replaceable, rechargeable or disposable.

Figure 7:
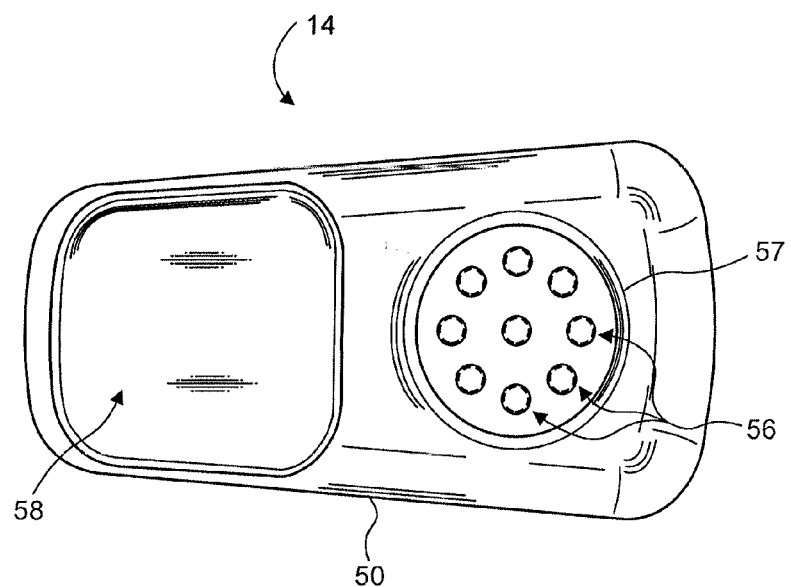
FIG. 7 is a bottom plan view of the monitor recorder of FIG. 4.

The monitor recorder 14 draws power externally from the battery provided in the non-conductive receptacle 25, thereby uniquely obviating the need for the monitor recorder 14 to carry a dedicated power source. FIG. 7 is a bottom plan view of the monitor recorder 14 of FIG. 4. A cavity 58 is formed on the bottom surface of the sealed housing 50 to accommodate the upward projection of the battery compartment 36 from the bottom surface of the non-conductive receptacle 25, when the monitor recorder 14 is secured in place on the non-conductive receptacle 25. A set of electrical contacts 56 protrude from the bottom surface of the sealed housing 50 and are arranged in alignment with the electrical pads 34 provided on the bottom surface of the non-conductive receptacle 25 to establish electrical connections between the electrode patch 15 and the monitor recorder 14. In addition, a seal coupling 57 circumferentially surrounds the set of electrical contacts 56 and securely mates with the moisture-resistant seal 35 formed on the bottom surface of the non-conductive receptacle 25. The battery contained within the battery compartment 36 can be replaceable, rechargeable or disposable. In a further embodiment, the ECG sensing circuitry of the monitor recorder 14 can be supplemented with additional sensors, including an $SpO_2$ sensor, a blood pressure sensor, a temperature sensor, respiratory rate sensor, a glucose sensor, an air flow sensor, and a volumetric pressure sensor, which can be incorporated directly into the monitor recorder 14 or onto the non-conductive receptacle 25.

The placement of the flexible backing 20 on the sternal midline 16 (or immediately to either side of the sternum 13) also helps to minimize the side-to-side movement of the wearable monitor 12 in the left- and right-handed directions during wear. However, the wearable monitor 12 is still susceptible to pushing, pulling, and torqueing movements, including compressional and torsional forces when the patient bends forward, and tensile and torsional forces when the patient leans backwards or twists. To counter the dislodgment of the flexible backing 20 due to compressional and torsional forces, a layer of non-irritating adhesive, such as hydrocolloid, is provided at least partially on the underside, or contact, surface of the flexible backing 20, but only on the distal end 30 and the proximal end 31. As a result, the underside, or contact surface of the longitudinal midsection 23 does not have an adhesive layer and remains free to move relative to the skin. Thus, the longitudinal midsection 23 forms a crimp relief that, respectively, facilitates compression and twisting of the flexible backing 20 in response to compressional and torsional forces. Other forms of flexible backing crimp reliefs are possible.

Figure 8:
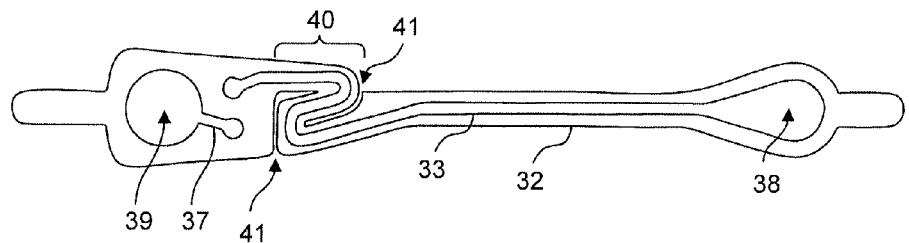
FIG. 8 is a top view showing the flexible circuit of the extended wear electrode patch of FIG. 4.

Unlike the flexible backing 20, the flexible circuit 32 can only bend and cannot stretch in a planar direction. The flexible circuit 32 can be provided either above or below the flexible backing 20. FIG. 8 is a top view showing the flexible circuit 32 of the extended wear electrode patch 15 of FIG. 4 when mounted above the flexible backing 20. A distal ECG electrode 38 and proximal ECG electrode 39 are respectively coupled to the distal and proximal ends of the flexible circuit 32 to serve as electrode signal pickups. The flexible circuit 32 preferably does not extend to the outside edges of the flexible backing 20, thereby avoiding gouging or discomforting the patient's skin during extended wear, such as when sleeping on the side. During wear, the ECG electrodes 38, 39 must remain in continual contact with the skin. A strain relief 40 is defined in the flexible circuit 32 at a location that is partially underneath the battery compartment 36 when the flexible circuit 32 is affixed to the flexible backing 20. The strain relief 40 is laterally extendable to counter dislodgment of the ECG electrodes 38, 39 due to bending, tensile, and torsional forces. A pair of strain relief cutouts 41 partially extend transversely from each opposite side of the flexible circuit 32 and continue longitudinally towards each other to define in 'S'-shaped pattern, when viewed from above. The strain relief, respectively, facilitates longitudinal extension and twisting of the flexible circuit 32 in response to tensile and torsional forces. Other forms of circuit board strain relief are possible.

Figure 9:
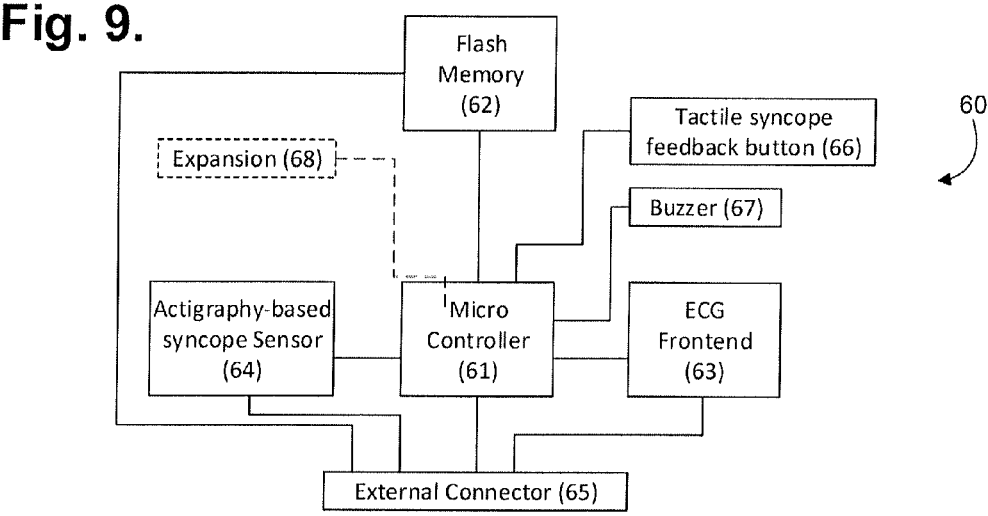
FIG. 9 is a functional block diagram showing the component architecture of the circuitry of the monitor recorder of FIG. 4.

ECG monitoring and other functions performed by the monitor recorder 14 are provided through a micro controlled architecture. FIG. 9 is a functional block diagram showing the component architecture of the circuitry 60 of the monitor recorder 14 of FIG. 4. The circuitry 60 is externally powered through a battery provided in the non-conductive receptacle 25, as further described with reference to FIG. 6. Both power and raw ECG signals, which originate in the pair of ECG electrodes 38, 39, as further described with reference to FIG. 8, on the distal and proximal ends of the electrode patch 15, are received through an external connector 65 that mates with a corresponding physical connector on the electrode patch 15. The external connector 65 includes the set of electrical contacts 56 that protrude from the bottom surface of the sealed housing 50 and that physically as well as electrically interface with the set of pads 34 provided on the bottom surface of the non-conductive receptacle 25. The external connector includes electrical contacts 56 for data download, microcontroller communications, power, analog inputs, and a peripheral expansion port. The arrangement of the pins on the electrical connector 65 of the monitor recorder 14 and the device into which the monitor recorder 14 is attached, whether an electrode patch 15 or a download station (not shown), follow the same electrical pin assignment convention to facilitate interoperability. The external connector 65 also serves as a physical interface to a download station that permits the retrieval of stored ECG monitoring data, communication with the monitor recorder 14, and performance of other functions. The download station is further described infra with reference to FIG. 18.

Operation of the circuitry 60 of the monitor recorder 14 is managed by a microcontroller 61, such as the EFM32 Tiny Gecko 32-bit microcontroller, manufactured by Silicon Laboratories Inc., Austin, Tex. The microcontroller 61 has flexible energy management modes and includes a direct memory access controller and built-in analog-to-digital and digital-to-analog converters (ADC and DAC, respectively). The microcontroller 61 also includes a program memory unit containing internal flash memory that is readable and writeable. The internal flash memory can also be programmed externally. The microcontroller 61 operates under modular micro program control as specified in firmware stored in the internal flash memory. The functionality and firmware modules relating to signal processing by the microcontroller 61 are further described infra with reference to FIG. 17. The microcontroller 61 draws power externally from the battery provided on the electrode patch 15 via a pair of the electrical contacts 56. The microcontroller 61 connects to the ECG front end circuit 63 that measures raw cutaneous electrical signals using a driven reference that eliminates common mode noise, as further described infra with reference to FIG. 12.

The circuitry 60 of the monitor recorder 14 also includes a flash memory 62, which the microcontroller 61 uses for storing ECG monitoring data as well as other physiology and information. The flash memory 62 also draws power externally from the battery provided on the electrode patch 15 via a pair of the electrical contacts 56. Data is stored in a serial flash memory circuit, which supports read, erase, and program operations over a communications bus. The flash memory 62 enables the microcontroller 61 to store digitized ECG data. The communications bus further enables the flash memory 62 to be directly accessed externally over the external connector 65 when the monitor recorder 14 is interfaced to a download station.

Figure 17:
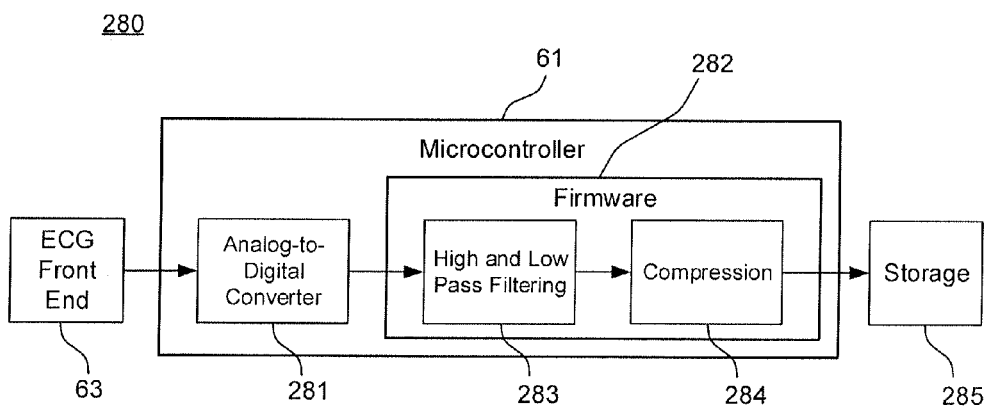
FIG. 17 is a functional block diagram showing the signal processing functionality of the microcontroller.

The microcontroller 61 includes functionality that enables the acquisition of samples of analog ECG signals, which are converted into a digital representation, as further described infra with reference to FIG. 17. In one mode, the microcontroller 61 will acquire, sample, digitize, signal process, and store digitized ECG data into available storage locations in the flash memory 62 until all memory storage locations are filled, after which the digitized ECG data needs to be downloaded or erased to restore memory capacity. Data download or erasure can also occur before all storage locations are filled, which would free up memory space sooner, albeit at the cost of possibly interrupting monitoring while downloading or erasure is performed. In another mode, the microcontroller 61 can include a loop recorder feature that will overwrite the oldest stored Syncodata once all storage locations are filled, albeit at the cost of potentially losing the stored data that was overwritten, if not previously downloaded. Still other modes of data storage and capacity recovery are possible.

Syncope episodes are associated with certain movements. For example, a patient experiencing a syncope episode, if standing and unassisted, is likely to fall down. Similarly, a patient who is sitting down, is likely to experience a sudden postural change when experiencing a syncope episode, such as falling back, forward, or to a side. The recognition of such movements through changes of acceleration and deceleration in the body can be used to detect syncope events. The circuitry 60 of the monitor recorder 14 further contains a syncope sensor implemented as at least one of an actigraphy-based syncope sensor 64, which is a 3-axis accelerometer in one embodiment, and a tactile syncope feedback button 66, as discussed infra. The accelerometer may be configured to generate interrupt signals to the microcontroller 61 upon detecting independent movement events, such as free-fall or waking up, and device position. In addition, the actigraphy provided by the accelerometer can be used during post-monitoring analysis to correct the orientation of the monitor recorder 14 if, for instance, the monitor recorder 14 has been inadvertently installed upside down, that is, with the monitor recorder 14 oriented on the electrode patch 15 towards the patient's feet, as well as for other event analyses.

In one embodiment, the accelerometer of actigraphy-based syncope sensor 64 may be configured with actigraphy-filtering criteria, and based on these criteria, the sensor only records actigraphy data that indicate a syncope event, such as a fall or sudden postural change. For example, when a patient is standing, an accelerometer records a g-force (g) equivalent to 1 g along the axis perpendicular towards the earth. If the patient falls, the accelerometer records a g-force equivalent to zero or very close to zero along the axis perpendicular towards the earth during the freefall, and the actigraphy-filtering criteria may identify such data as an impulse that exceeds a certain impulse threshold. A syncope event may also be consistent with a sudden acceleration or deceleration that indicates a sudden postural change, where the g-force along at least one axis is greater than a specific limit, which the actigraphy-filtering criteria may also identify as an impulse that exceeds a certain impulse threshold. In a further embodiment, the actigraphy-based syncope sensor 64 may be configured with actigraphy filtering criteria that permit the sensor to record a broader range of actigraphy data, such as data that indicate multiple notable physical events. Such events may include, for example, falling, a sudden postural change, sleeping, waking, and hyperactivity, which may be distinguished from actigraphy data that reflect the rise and fall of a patient's chest during regular breathing, which is ordinary and expected. Other embodiments are possible, wherein different types of actigraphy data are collected.

Further, the circuitry 60 of the monitor recorder 14 includes patient-interfaceable components, including the tactile syncope feedback button 66, which a patient can press to indicate a syncope episode or to perform other functions. For example, the patient 10, 11 can press the tactile syncope feedback button 66 at onset or shortly after a syncope episode, allowing for detection of a syncope event even if the patient's posture does not change, such as if the patient is lying down. Other patient-interfaceable components can include a buzzer 67, such as a speaker, magnetic resonator, or piezoelectric buzzer. The buzzer 67 can be used by the microcontroller 61 to output feedback to a patient, such as to confirm power up and initiation of ECG monitoring. Still other components as part of the circuitry 60 of the monitor recorder 14 are possible.

The microcontroller 61 includes an expansion port 68 that also utilizes the communications bus. External devices, separately drawing power externally from the battery provided on the electrode patch 15 or other source, can interface to the microcontroller 61 over the expansion port 68 in half duplex mode. For instance, an external physiology sensor can be provided as part of the circuitry 60 of the monitor recorder 14 or can be provided on the electrode patch 15 with communication with the microcontroller 61 provided over one of the electrical contacts 56. The physiology sensor can include an $SpO_2$ sensor, blood pressure sensor, temperature sensor, respiratory rate sensor, glucose sensor, airflow sensor, volumetric pressure sensing, or other types of sensor or telemetric input sources. In a further embodiment, a wireless interface for interfacing with other wearable (or implantable) physiology monitors, data offload, and programming can be provided as part of the circuitry 60 of the monitor recorder 14 or can be provided on the electrode patch 15 with communication with the microcontroller 61 provided over one of the electrical contacts 56.

Figure 10:
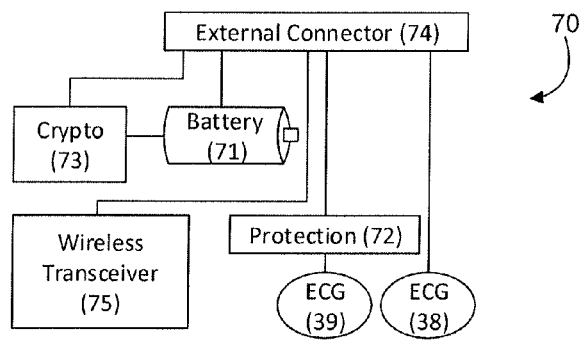
FIG. 10 is a functional block diagram showing the circuitry of the extended wear electrode patch of FIG. 4.

While the monitor recorder 14 operates under micro control, most of the electrical components of the electrode patch 15 operate passively. FIG. 10 is a functional block diagram showing the circuitry 70 of the extended wear electrode patch 15 of FIG. 4. The circuitry 70 of the electrode patch 15 is electrically coupled with the circuitry 60 of the monitor recorder 14 through an external connector 74. The external connector 74 is terminated through the set of pads 34 provided on the bottom of the non-conductive receptacle 25, which electrically mate to corresponding electrical contacts 56 protruding from the bottom surface of the sealed housing 50 to electrically interface the monitor recorder 14 to the electrode patch 15.

The circuitry 70 of the electrode patch 15 performs three primary functions. First, a battery 71 is provided in a battery compartment formed on the bottom surface of the non-conductive receptacle 25. The battery 71 is electrically interfaced to the circuitry 60 of the monitor recorder 14 as a source of external power. The unique provisioning of the battery 71 on the electrode patch 15 provides several advantages. First, placing the battery 71 physically on the electrode patch 15 lowers the center of gravity of the overall wearable monitor 12 and, thereby, helps to minimize shear forces as well as the effects of movements of the patient and clothing. Moreover, the housing 50 of the monitor recorder 14 is sealed against moisture, and providing power externally avoids having to either periodically open the housing 50 for the battery replacement, which also creates the potential for moisture intrusion and human error, or to recharge the battery, which can potentially take the monitor recorder 14 off line for hours at a time. In addition, the electrode patch 15 is intended to be disposable, while the monitor recorder 14 is a reusable component. Each time that the electrode patch 15 is replaced, a fresh battery is provided for the use of the monitor recorder 14, which enhances ECG monitoring performance quality and duration of use. Further, the architecture of the monitor recorder 14 is open such that other physiology sensors or components can be added using the expansion port 68 of the microcontroller 61. Requiring those additional sensors or components to draw power from a source external to the monitor recorder 14 renders power considerations independent of the monitor recorder 14. This approach also enables a battery of higher capacity to be introduced when needed to support the additional sensors or components without effecting the monitor recorders circuitry 60.

Second, the pair of ECG electrodes 38, 39, respectively, provided on the distal and proximal ends of the flexible circuit 32 are electrically coupled to the set of pads 34 provided on the bottom of the non-conductive receptacle 25 by way of their respective circuit traces 33, 37. The signal ECG electrode 39 includes a protection circuit 72, which is an inline resistor that protects the patient from excessive leakage current should the front end circuit fail.

Last, in a further embodiment, the circuitry 70 of the electrode patch 15 includes a cryptographic circuit 73 to authenticate an electrode patch 15 for use with a monitor recorder 14. The cryptographic circuit 73 includes a device capable of secure authentication and validation. The cryptographic device 73 ensures that only genuine, non-expired, safe, and authenticated electrode patches 15 are permitted to provide monitoring data to a monitor recorder 14 and for a specific patient.

Figure 11:
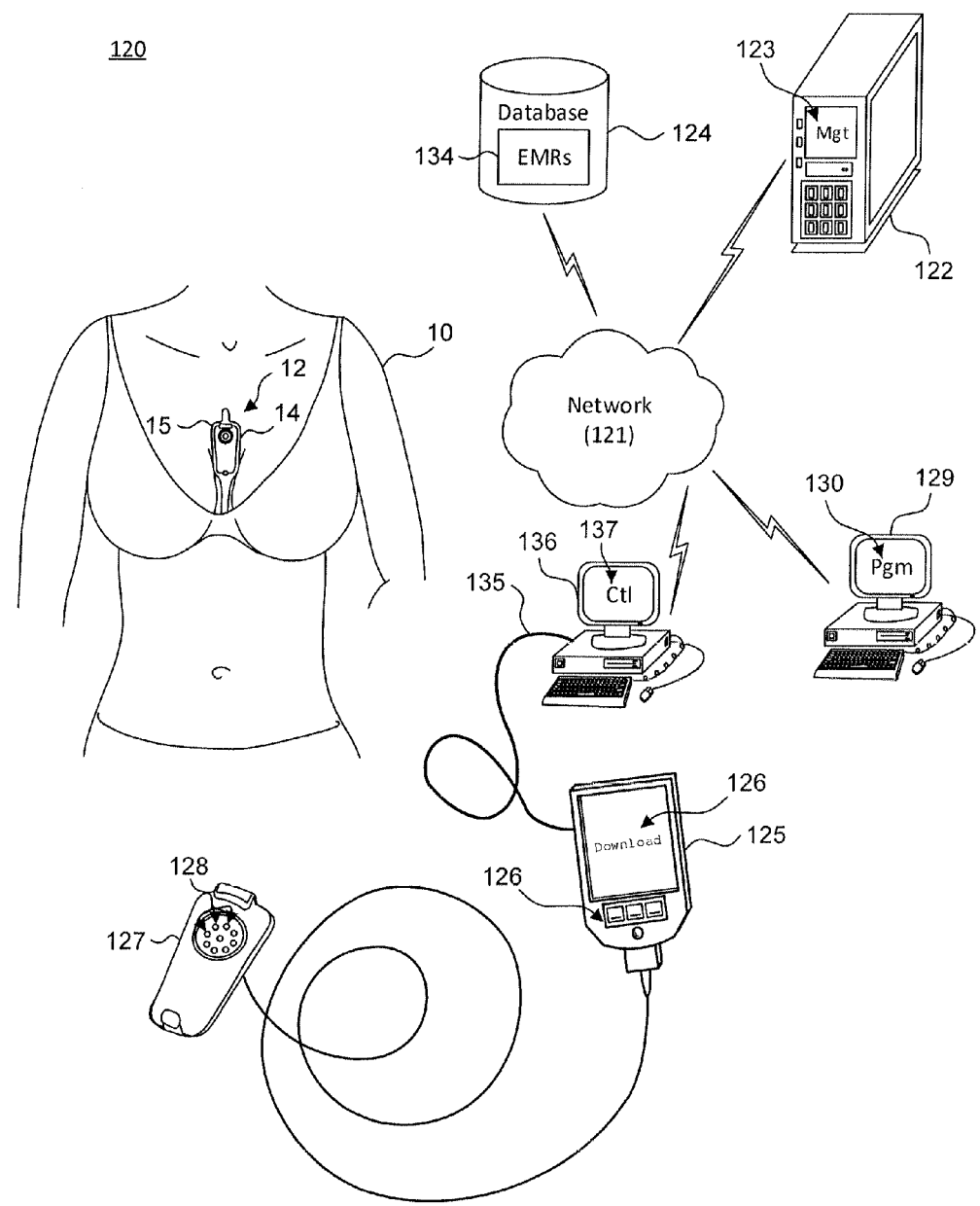
FIG. 11 is a functional block diagram showing a system for remote interfacing of a combined ECG and syncope sensor monitor recorder in accordance with one embodiment.

When operated standalone, the monitor recorder 14 of the wearable monitor 12 senses and records the patient's ECG data into an onboard memory. FIG. 11 is a functional block diagram showing a system 120 for remote interfacing of a combined ECG and syncope sensor monitor recorder in accordance with one embodiment. The monitor recorder 14 is a reusable component that can be fitted during patient monitoring into a non-conductive receptacle provided on the electrode patch 15, as further described infra with reference to FIG. 4, and later removed for offloading stored ECG data or to receive revised programming. The monitor recorder 14 can then be connected to a download station 125, which could be a programmer or other device that permits the retrieval of stored ECG monitoring data, execution of diagnostics on or programming of the monitor recorder 14, or other functions. The monitor recorder 14 includes a set of electrical contacts (not shown) that enable the monitor recorder 14 to physically interface with a set of terminals 128 on a paired receptacle 127 of the download station 125. In turn, the download station 125 executes a communications or offload program 126 ("Offload") or similar program that interacts with the monitor recorder 14 via the physical interface to retrieve the stored ECG monitoring data or to execute diagnostics on or reprogram the monitor recorder's program memory unit and, thereby, revise the subsequent operation of the monitor recorder 14. The download station 125 could be a server, personal computer, tablet or handheld computer, smart mobile device, or purpose-built programmer designed specifically to interface with a monitor recorder 14. Still other forms of download station 125 are possible. In addition, the wearable monitor 12 can interoperate with other devices, as further described in detail in commonly-assigned U.S. patent application, entitled "Remote Interfacing of Extended Wear Electrocardiography and Physiological Sensor Monitor," Ser. No. 14/082,071, filed Nov. 15, 2013, pending, the disclosure of which is incorporated by reference.

Figure 15:
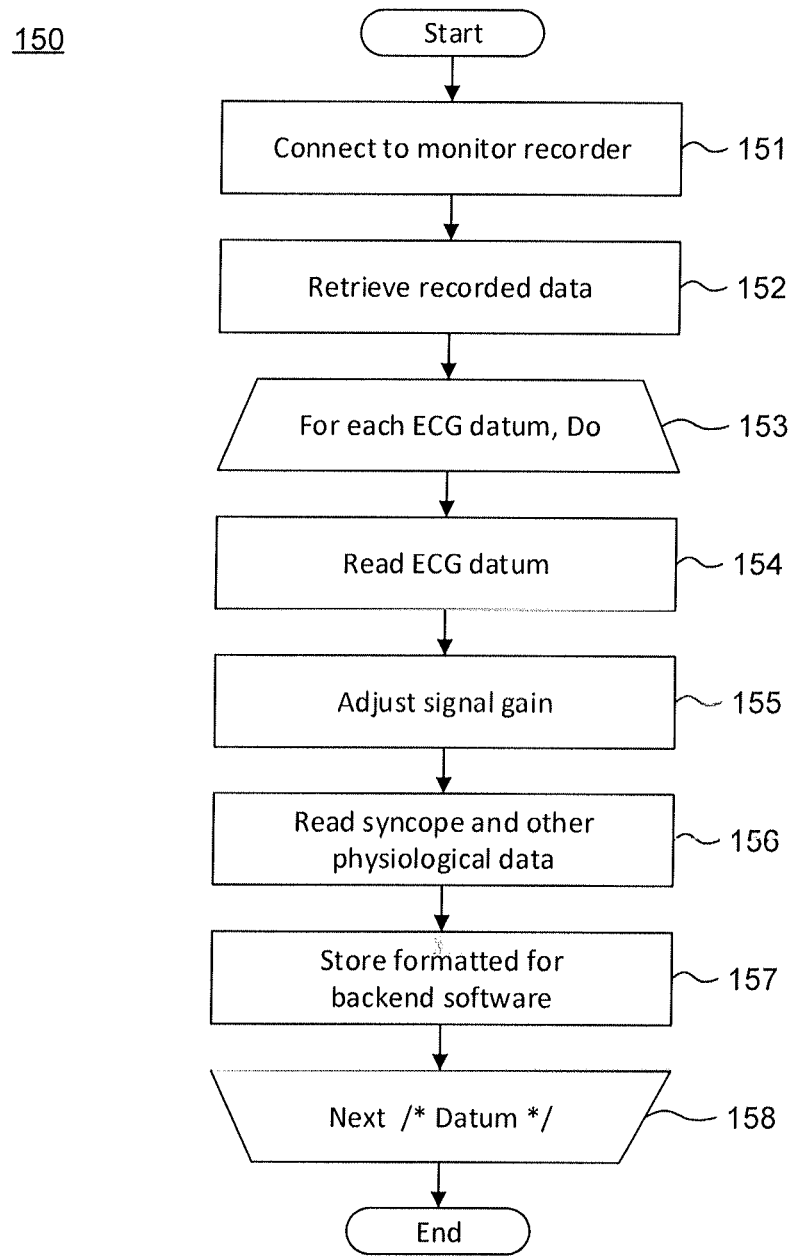
FIG. 15 is a flow diagram showing a method for offloading and converting ECG and other physiological data from an ambulatory extended-wear electrocardiography and syncope sensor monitor in accordance with one embodiment.

Upon retrieving stored ECG monitoring data from a monitor recorder 14, middleware first operates on the retrieved data to adjust the ECG capture quality, as necessary, and to convert the retrieved data into a format suitable for use by third party post-monitoring analysis software, as further described infra with reference to FIG. 15. The formatted data can then be retrieved from the download station 125 over a hard link 135 using a control program 137 ("Ctl") or analogous application executing on a personal computer 136 or other connectable computing device, via a communications link (not shown), whether wired or wireless, or by physical transfer of storage media (not shown). The personal computer 136 or other connectable device may also execute middleware that converts ECG data and other information into a format suitable for use by a third-party post-monitoring analysis program, as further described infra with reference to FIG. 15. Note that formatted data stored on the personal computer 136 would have to be maintained and safeguarded in the same manner as electronic medical records (EMRs) 134 in the secure database 124, as further discussed infra. In a further embodiment, the download station 125 can directly interface with other devices over a computer communications network 121, which could be a combination of a local area network and a wide area network, including the Internet, over a wired or wireless connection.

A client-server model could be used to employ a server 122 to remotely interface with the download station 125 over the network 121 and retrieve the formatted data or other information. The server 122 executes a patient management program 123 ("Mgt") or similar application that stores the retrieved formatted data and other information in a secure database 124 cataloged in that patient's EMRs 134. In addition, the patient management program 123 could manage a subscription service that authorizes a monitor recorder 14 to operate for a set period of time or under pre-defined operational parameters, such as described in commonly-assigned U.S. patent application, entitled "Self-Authenticating Electrocardiography Monitoring Circuit," Ser. No. 14/082,066, filed Nov. 15, 2013, pending, the disclosure of which is incorporated by reference.

The patient management program 123, or other trusted application, also maintains and safeguards the secure database 124 to limit access to patient EMRs 134 to only authorized parties for appropriate medical or other uses, such as mandated by state or federal law, such as under the Health Insurance Portability and Accountability Act (HIPAA) or per the European Union's Data Protection Directive. For example, a physician may seek to review and evaluate his patient's ECG monitoring data, as securely stored in the secure database 124. The physician would execute an application program 130 ("Pgm"), such as a post-monitoring ECG analysis program, on a personal computer 129 or other connectable computing device, and, through the application 130, coordinate access to his patient's EMRs 134 with the patient management program 123. Other schemes and safeguards to protect and maintain the integrity of patient EMRs 134 are possible.

Figure 12:
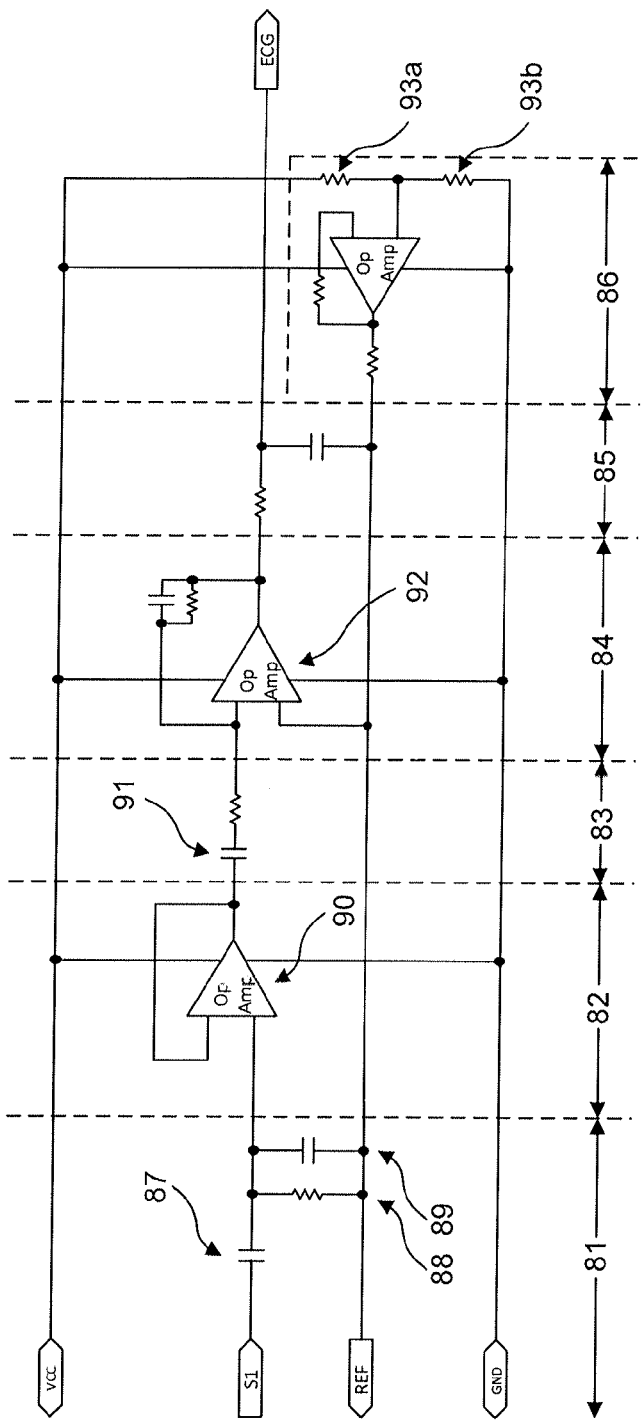
FIG. 12 is a schematic diagram showing the ECG front end circuit of the circuitry of the monitor recorder of FIG. 9.

The ECG front end circuit 63 measures raw cutaneous electrical signals using a driven reference that effectively reduces common mode noise, power supply noise and system noise, which is critical to preserving the characteristics of low-amplitude cardiac action potentials, especially those signals from the atria. FIG. 12 is a schematic diagram 80 showing the ECG front end circuit 63 of the circuitry 60 of the monitor recorder 14 of FIG. 9. The ECG front end circuit 63 senses body surface potentials through a signal lead ("S1") and reference lead ("REF"), which are, respectively, connected to the ECG electrodes of the electrode patch 15. Power is provided to the ECG front end circuit 63 through a pair of DC power leads ("VCC" and "GND"). An analog ECG signal ("ECG") representative of the electrical activity of the patient's heart over time is output, which the micro controller 11 converts to digital representation and filters, as further described infra.

The ECG front end circuit 63 is organized into five stages, a passive input filter stage 81, a unity gain voltage follower stage 82, a passive high-pass filtering stage 83, a voltage amplification and active filtering stage 84, and an anti-aliasing passive filter stage 85, and includes a reference generator. Each of these stages and the reference generator will now be described.

The passive input filter stage 81 includes the parasitic impedance of the ECG electrodes 38, 39, as further described with reference to FIG. 8, the protection resistor that is included as part of the protection circuit 72 of the ECG electrode 39, as further described with reference to FIG. 10, an AC coupling capacitor 87, a termination resistor 88, and filter capacitor 89. This stage passively shifts the frequency response poles downward there is a high electrode impedance from the patient on the signal lead S1 and reference lead REF, which reduces high-frequency noise.

The unity gain voltage follower stage 82 provides a unity voltage gain that allows current amplification by an Operational Amplifier ("Op Amp") 90. In this stage, the voltage stays the same as the input, but more current is available to feed additional stages. This configuration allows a very high input impedance to avoid disrupting the body surface potentials or the filtering effect of the previous stage.

The passive high-pass filtering stage 83 is a high-pass filter that removes baseline wander and any offset generated from the previous stage. Adding an AC coupling capacitor 91 after the Op Amp 90 allows the use of lower cost components, while increasing signal fidelity.

The voltage amplification and active filtering stage 84 amplifies the voltage of the input signal through Op Amp 91, while applying a low-pass filter. The DC bias of the input signal is automatically centered in the highest performance input region of the Op Amp 91 because of the AC coupling capacitor 91.

The anti-aliasing passive filter stage 85 provides an anti-aliasing low-pass filter. When the microcontroller 61 acquires a sample of the analog input signal, a disruption in the signal occurs as a sample and hold capacitor that is internal to the microcontroller 61 is charged to supply a signal for acquisition.

The reference generator in subcircuit 86 drives a driven reference containing power supply noise and system noise to the reference lead REF. A coupling capacitor 87 is included on the signal lead S1, and a pair of resistors 93a, 93b inject system noise into the reference lead REF. The reference generator is connected directly to the patient, thereby avoiding the thermal noise of the protection resistor that is included as part of the protection circuit 72.

In contrast, conventional ECG lead configurations attempt to balance signal and reference lead connections. The conventional approach suffers from the introduction of differential thermal noise, lower input common mode rejection, increased power supply noise, increased system noise, and differential voltages between the patient reference and the reference used on the device that can obscure, at times, extremely low-amplitude body surface potentials.

Here, the parasitic impedance of the ECG electrodes 38, 39; the protection resistor that is included as part of the protection circuit 72; and the coupling capacitor 87 allow the reference lead REF to be connected directly to the skin's surface without any further components. As a result, the differential thermal noise problem caused by pairing protection resistors to signal and reference leads, as used in conventional approaches, is avoided.

The microcontroller 61 operates under modular microprogram control as specified in firmware, and the program control includes processing of the analog ECG signal output by the ECG front end circuit 63. FIG. 17 is a functional block diagram showing the signal processing functionality 280 of the microcontroller 61. The microcontroller 61 operates under modular microprogram control as specified in firmware 282. The firmware modules 282 include high- and low-pass filtering 283 as well as compression 284. Other modules are possible. The microcontroller 61 has a built-in ADC; however, ADC functionality could also be provided in the firmware 282.

The ECG front end circuit 63 first outputs an analog ECG signal, which the ADC 281 acquires, samples and converts into an uncompressed digital representation. The microcontroller 61 includes one or more firmware modules 283 that perform filtering. In one embodiment, three low-pass filters and two high-pass filters are used. Following filtering, the digital representation of the cardiac activation wave front amplitudes are compressed by a compression module 284 before being written out to storage 285.

Figure 18:
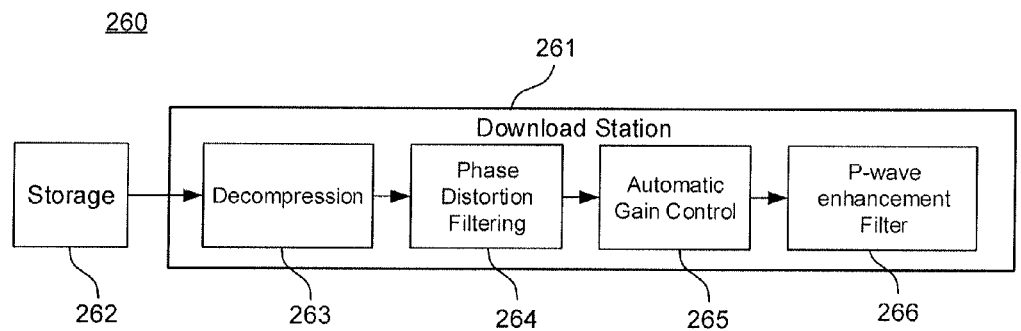
FIG. 18 is a functional block diagram showing the operations performed by the download station.

The download station executes a communications or offload program ("Offload") or similar program that interacts with the monitor recorder 14 via the external connector 65 to retrieve the stored ECG monitoring data. FIG. 18 is a functional block diagram showing the operations 260 performed by the download station. The download station could be a server, personal computer, tablet or handheld computer, smart mobile device, or purpose-built programmer designed specifically for interfacing with a monitor recorder 14. Still other forms of download station are possible, including download stations connected through wireless interfacing using, for instance, a smart phone connected to the monitor recorder 14 through Bluetooth or Wi-Fi.

The download station is responsible for offloading stored ECG monitoring data from a monitor recorder 14 and includes an electromechanical docking interface by which the monitor recorder 14 is connected at the external connector 65. The download station operates under programmable control as specified in software 261. The stored ECG monitoring data retrieved from storage 262 on a monitor recorder 14 are first decompressed by a decompression module 263, which converts the stored ECG monitoring data back into an uncompressed digital representation more suited to signal processing than a compressed signal. The retrieved ECG monitoring data may be stored into local storage for archival purposes, either in original compressed form or uncompressed.

The download station can include an array of filtering modules. For instance, a set of phase distortion filtering tools 264 may be provided, where corresponding software filters can be provided for each filter implemented in the firmware executed by the microcontroller 61. The digital signals are run through the software filters in a reverse direction to remove phase distortion. For instance, a 45 Hertz high-pass filter in firmware may have a matching reverse 45 Hertz high-pass filter in software. Most of the phase distortion is corrected, that is, canceled to eliminate noise at the set frequency, but data at other frequencies in the waveform remain unaltered. As well, bidirectional impulse infinite response (IIR) high-pass filters and reverse direction (symmetric) IIR low-pass filters can be provided. Data is run through these filters first in a forward direction, then in a reverse direction, which generates a square of the response and cancels out phase distortion. This type of signal processing is particularly helpful with improving the display of the ST-segment by removing low-frequency noise.

An automatic gain control (AGC) module 265 can also be provided to adjust the digital signals to a usable level based on peak or average signal level or other metric. AGC is particularly critical to single-lead ECG monitors, where physical factors, such as the tilt of the heart, can affect the electrical field generated. On three-lead Holter monitors, the leads are oriented in vertical, horizontal and diagonal directions. As a result, the horizontal and diagonal leads may be higher amplitude and ECG interpretation will be based on one or both of the higher amplitude leads. In contrast, the wearable monitor 12 has only a single lead that is oriented in the vertical direction; thus, variations in amplitude will be wider than available with multi-lead monitors, which have alternate leads to fall back upon.

In addition, AGC may be necessary to maintain compatibility with existing ECG interpretation software, which is typically calibrated for multi-lead ECG monitors for viewing signals over a narrow range of amplitudes. Through the AGC module 265, the gain of signals recorded by the monitor recorder 14 of the wearable monitor 12 can be attenuated up (or down) to work with an FDA-approved, commercially available ECG interpretation.

AGC can be implemented in a fixed fashion that is uniformly applied to all signals in an ECG recording, adjusted as appropriate on a recording-by-recording basis. Typically, a fixed AGC value is calculated based on how an ECG recording is received to preserve the amplitude relationship between the signals. Alternatively, AGC can be varied dynamically throughout an ECG recording, where signals in different segments of an ECG recording are amplified up (or down) by differing amounts of gain.

Typically, the monitor recorder 14 will record a high resolution, low-frequency signal for the P-wave segment. However, for some patients, the result may still be a visually small signal. Although high resolution is present, the unaided eye will normally be unable to discern the P-wave segment. Therefore, gaining the signal is critical to visually depicting P-wave detail. This technique works most efficaciously with a raw signal with low noise and high resolution, as generated by the monitor recorder 14. Automatic gain control applied to a high noise signal will only exacerbate noise content and be self-defeating.

Finally, the download station can include filtering modules specifically intended to enhance P-wave content. For instance, a P-wave base boost filter 266, which is a form of pre-emphasis filter, can be applied to the signal to restore missing frequency content or to correct phase distortion. Still other filters and types of signal processing are possible.

Figure 13:
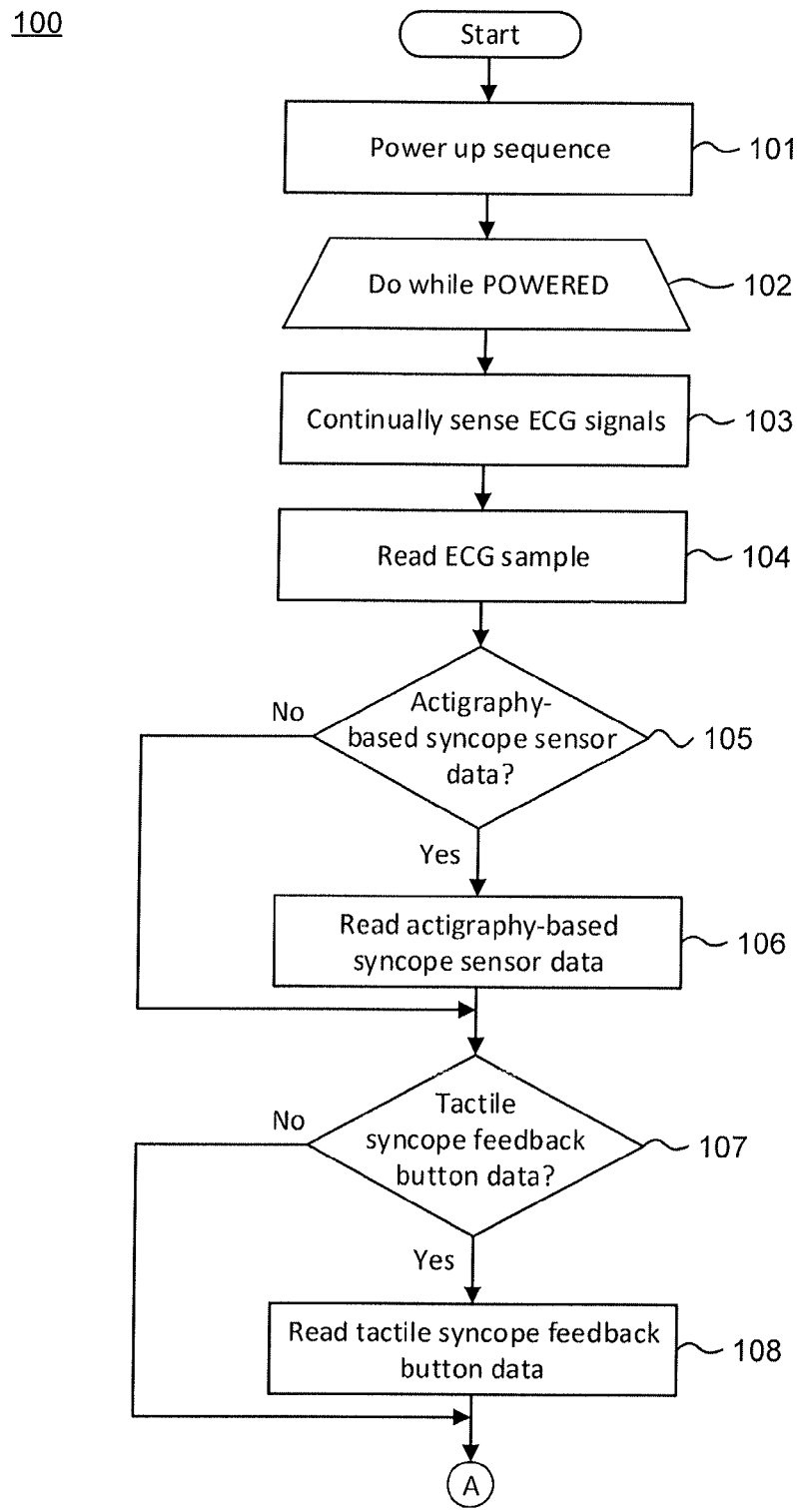
FIG. 13 is a flow diagram showing a monitor recorder-implemented method for monitoring ECG and syncope data for use in the monitor recorder of FIG. 4.

The monitor recorder 14 continuously monitors the patient's heart rate and physiology. FIG. 13 is a flow diagram showing a monitor recorder-implemented method 100 for monitoring ECG data and syncope data for use in the monitor recorder 14 of FIG. 4. Initially, upon being connected to the set of pads 34 provided with the non-conductive receptacle 25 when the monitor recorder 14 is snapped into place, the microcontroller 61 executes a power up sequence (step 101). During the power up sequence, the voltage of the battery 71 is checked, the state of the flash memory 62 is confirmed, both in terms of operability check and available capacity, and microcontroller operation is diagnostically confirmed. In a further embodiment, an authentication procedure between the microcontroller 61 and the electrode patch 15 are also performed.

Figure 14:
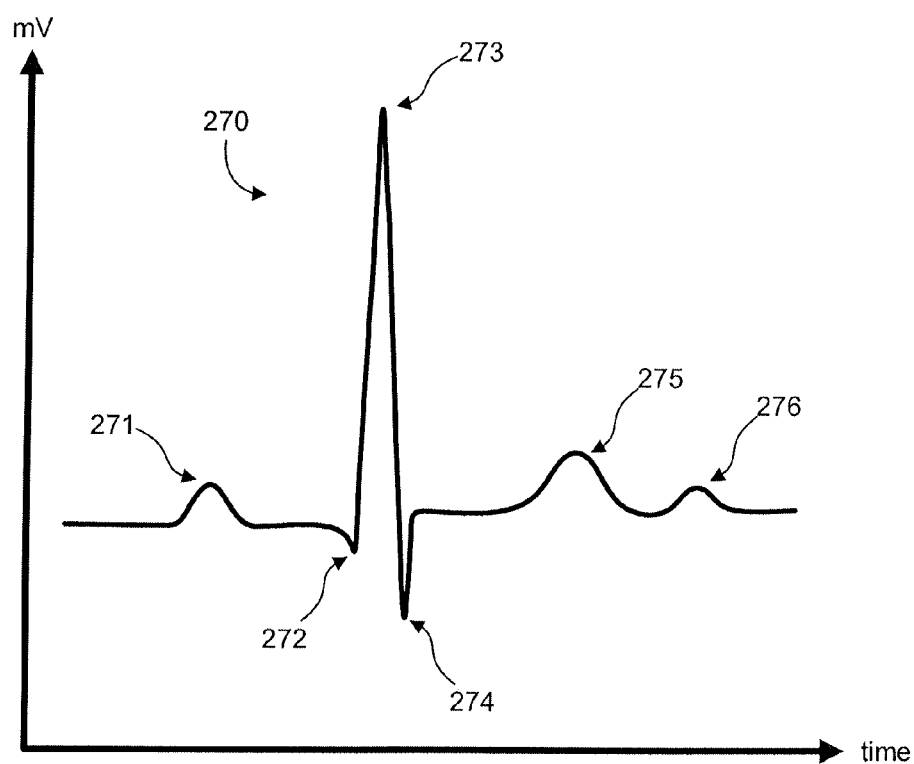
FIG. 14 is a graph showing, by way of example, a typical ECG waveform.

Following satisfactory completion of the power up sequence, an iterative processing loop (steps 102-113) is continually executed by the microcontroller 61. During each iteration (step 102) of the processing loop, the ECG frontend 63, as further described with reference to FIG. 9, continually senses the cutaneous ECG electrical signals (step 103) via the ECG electrodes 38, 29 and is optimized to maintain the integrity of the P-wave. A sample of the ECG signal is read (step 104) by the microcontroller 61 by sampling the analog ECG signal that is output by the ECG front end circuit 63. FIG. 14 is a graph showing, by way of example, a typical ECG waveform 270. The x-axis represents time in approximate units of tenths of a second. The y-axis represents cutaneous electrical signal strength in approximate units of millivolts. The P-wave 271 has a smooth, normally upward, that is, positive, waveform that indicates atrial depolarization. The QRS complex often begins with the downward deflection of a Q-wave 272 followed by a larger upward deflection of an R-wave 273 and is terminated with a downward waveform of the S-wave 274, collectively representative of ventricular depolarization. The T-wave 275 is normally a modest upward waveform, representative of ventricular depolarization, while the U-wave 276, often not directly observable, indicates the recovery period of the Purkinje conduction fibers.

Sampling the R-to-R interval enables heart rate information derivation. For instance, the R-to-R interval represents the ventricular rate and rhythm, while the P-to-P interval represents the atrial rate and rhythm. Importantly, the PR interval is indicative of atrioventricular (AV) conduction time, and abnormalities in the PR interval can reveal underlying heart disorders, which is another reason that the P-wave quality achievable by the ambulatory electrocardiography monitoring patch optimized for capturing low-amplitude cardiac action potential propagation described herein is medically unique and important. The long-term observation of these ECG indicia, as provided through extended wear of the wearable monitor 12, provides valuable insights into the patient's cardiac function symptoms and overall well-being.

Referring back to FIG. 13, the monitor recorder 14 also receives data from a syncope sensor. During each iteration (step 102) of the processing loop, the syncope sensor monitors a patient's movement as well as the presence of patient feedback from the tactile syncope feedback button 66 and detects if there is a syncope event, such as an event that is approximately coincident with a cardiovascular episode, that should be recorded as part of the monitoring. If a syncope event is detected through the actigraphy-based syncope sensor 64 (step 105), the actigraphy-based syncope sensor 64 provides a signal to the microprocessor 61, and the microprocessor 61 reads the data sample that includes the syncope event data (step 106). If a syncope event is detected through the tactile syncope feedback button 66 (step 107), the tactile syncope feedback button 66 provides a signal to the microprocessor 61, and the microprocessor 61 reads the syncope event data (step 108). If no such syncope events are detected, the method 100 proceeds to step 109. Each sampled ECG signal and any syncope event data in quantized and digitized form are temporarily staged in a buffer (step 109), pending compression preparatory to storage in the flash memory 62 (step 110). Following compression, the compressed ECG digitized sample and any syncope event data are again buffered (step 111), then written to the flash memory 62 (step 112) using the communications bus. Processing continues (step 113) so long as the monitoring recorder 14 remains connected to the electrode patch 15 (and storage space remains available in the flash memory 62), after which the processing loop is exited (step 113) and execution terminates. This design provides an automatic time-correlation between a syncope event and the corresponding ECG data. No additional software is needed to synchronize the syncope data and ECG data, resulting in an efficient monitor recorder 14 and simplified post-recording processing. Still other operations and steps are possible. In a further embodiment, the syncope event data are read and stored through a conceptually-separate execution thread as part of the iterative processing loop.

The monitor recorder 14 stores ECG data and other information in the flash memory subsystem 62, as further described with reference to FIG. 9, using a proprietary format that includes data compression. As a result, data retrieved from a monitor recorder 14 must first be converted into a format suitable for use by third party post-monitoring analysis software. FIG. 15 is a flow diagram showing a method 150 for offloading and converting ECG and other physiological data from of an ambulatory extended-wear electrocardiography and syncope sensor monitor in accordance with one embodiment. The method 150 can be implemented in software, and execution of the software can be performed on a download station 125, which could be a programmer, other device, or a computer system, including a server 122 or personal computer 129, such as further described supra with reference to FIG. 11, as a series of process or method modules or steps. For convenience, the method 150 will be described in the context of being performed by a personal computer 136 or other connectable computing device, as further described with reference to FIG. 11, as middleware that converts syncope and ECG data as well as other information into a format suitable for use by a third-party post-monitoring analysis program. Execution of the method 150 by another computer system or download station 125 would be analogous mutatis mutandis.

Initially, the download station 125 is connected to the monitor recorder 14 (step 151), such as by physically interfacing with a set of terminals 128 on a paired receptacle 127 or by a wireless connection, if available. The data stored on the monitor recorder 14, including ECG, physiological monitoring, and patient-mediated tactile feedback data, as well as other recorded data and other information are retrieved (step 152) over a hard link 135 using a control program 137 ("Ctl") or analogous application executing on a personal computer 136 or other connectable computing device.

The data retrieved from the monitor recorder 14 is in a proprietary storage format and each datum of recorded ECG monitoring data, as well as any other physiological data or other information, must be converted, so that the data can be used by a third-party post-monitoring analysis program. Each datum of ECG monitoring data is converted by the middleware (steps 153-158) in an iterative processing loop. During each iteration (step 153), the ECG datum is read (step 154) and, if necessary, the gain of the ECG signal is adjusted (step 155) to compensate, for instance, for relocation or replacement of the electrode patch 15 during the monitoring period. Filtering described below with reference to FIG. 18 can also optionally take place during step 155.

In addition, depending upon the configuration of the wearable monitor 12, other physiological data (or other information), including patient events, such as air flow events, fall, peak activity level, sleep detection, and detection of patient activity levels and states, may be recorded along with the ECG monitoring data, which is read (step 156) and time-correlated to the ECG monitoring. For instance, syncope data may have been collected by the patient-mediated syncope tactile feedback button 66 or the actigraphy-based syncope sensor 64 based on a sensed event, such as a sudden change in orientation due to the patient taking a fall or a sudden postural change. In response, the monitor recorder 14 will embed the syncope data into the stream of data, including ECG monitoring data, that are recorded to the flash memory 62 by the micro-controller 61. Post-monitoring, the syncope data are temporally matched to the ECG data to provide the proper physiological context to the sensed event. Additional types of processing for the other physiological data (or other information) are possible.

Thus, during execution of the middleware, any other physiological data (or other information) that has been embedded into the recorded ECG monitoring data are read (step 156) and time-correlated to the time frame of the ECG signals that occurred at the time that the other physiological data (or other information) were noted. Finally, the ECG datum, for which the signal gain has been adjusted, if appropriate, and other physiological data, if applicable and as time-correlated, are stored in a format suitable to the backend software (step 157) used in post-monitoring analysis.

In a further embodiment, the other physiological data, if apropos, are embedded within an unused ECG track. For example, the SCP-ENG standard allows multiple ECG channels to be recorded into a single ECG record. However, the monitor recorder 14 only senses one ECG channel. The other physiological data can be stored into an additional ECG channel, which would otherwise be zero-padded or altogether omitted. One example of the other physiological data is actigraphy data. The backend software would then be able to read the other physiological data in context with the single channel of ECG monitoring data recorded by the monitor recorder 14, provided the backend software implemented changes necessary to interpret the other physiological data. Still other forms of embedding the other physiological data with formatted ECG monitoring data or providing the other physiological data in a separate manner are possible. Processing continues (step 158) for each remaining ECG datum, after which the processing loop is exited and execution terminates. Still other operations and steps are possible.

Figure 16:
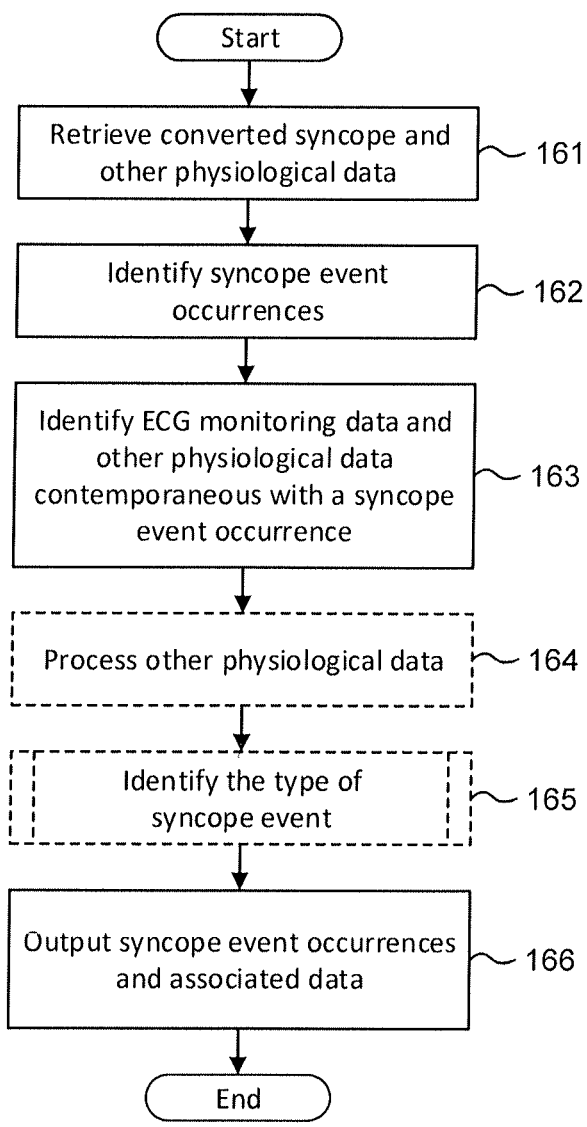
FIG. 16 is a method for processing data collected by the combined ECG and syncope monitor in accordance with one embodiment

The collection of the ECG data as described above and as described in a commonly assigned U.S. patent application, entitled "Extended Wear Ambulatory Electrocardiography and Physiological Sensor Monitor," Ser. No. 14/080,725, filed Nov. 14, 2013, pending, the disclosure of which is incorporated by reference, allows acquisition of ECG data collected over an extended period of time and, when combined the recording of syncope events, simplifies monitoring for episodes of cardiac-based and other syncope conditions. The occurrence of syncope events and ECG data are monitored by the monitor recorder 14 through the syncope sensor. The data collected by the monitor recorder 14 can be further processed by the application software to correlate the syncope data with ECG and other physiological data, if applicable. FIG. 16 is a flow diagram showing a method 160 for processing syncope data collected by a monitor recorder 14 in accordance with one embodiment. The converted syncope data include patient-mediated tactile feedback and actigraphy-based syncope data and other physiological data, including ECG monitoring. The converted syncope and other physiological data are offloaded and converted as described supra with reference to FIG. 15. The converted syncope and other physiological data are then retrieved by the backend software (step 161). The backend software processes the retrieved physiological data to identify the data regarding syncope events, which include data from the tactile syncope feedback button 66 and the data from the actigraphy-based syncope sensor 66 that are indicative of a fall or postural change (step 162). For instance, a common cause for cardiac-based syncope, cardiac arrhythmias are defined by P-wave morphology and their relationship to QRS intervals. For instance, atrial fibrillation (AF), an abnormally rapid heart rhythm, can be confirmed by the presence of erratic atrial activity or the absence of distinct P-waves and an irregular ventricular rate. Atrial flutter can be diagnosed with characteristic "sawtooth" P-waves often occurring twice for each QRS wave. Some congenital supraventricular tachycardias, like AV node re-entry and atrioventricular reentrant tachycardia using a concealed bypass tract, are characterized by an inverted P-wave occurring shortly after the QRS wave. Similarly, a sinoatrial block is characterized by a delayed onset of P-waves, while a junctional rhythm, which is an abnormal heart rhythm due impulses from tissue located in the AV node area, usually presents without P-waves or with inverted P-waves within or shortly before or after the QRS wave. Further, P-wave amplitudes are valuable for diagnosis. The presence of broad, notched P-waves can indicate left atrial enlargement or disease. Conversely, the presence of tall, peaked P-waves, especially in the initial half, can indicate right atrial enlargement. Finally, P-waves with increased amplitude can indicate hypokalemia, which is caused by low blood potassium, whereas P-waves with decreased amplitude can indicate hyperkalemia, which is caused by elevated blood potassium. P-wave analyses are also used in diagnosing other medical disorders, including blood chemistry imbalance.

Both the occurrence of a syncope event and the patient's ECG monitoring data as well as any other available physiological data that may be of diagnostic interest are identified (step 163).

Other types of physiological data may include data recorded by other physiology sensors, including the $SpO_2$ sensor, blood pressure sensor, temperature sensor, glucose sensor, airflow sensor, volumetric pressure sensing, or other types of sensor or telemetric input sources. In this example, if a blood pressure sensor were available to record blood pressure substantially concurrent to monitoring ECG and syncope data, the retrieved blood pressure data would be temporally aligned with the syncope and other physiological data relating to the patient's syncope event and, thereby, aid in diagnostic efficacy. Blood pressure recorded by a blood pressure sensor may provide the proper physiological context to the sensed event because other physiological events may be used to aid in distinguishing certain true syncope events from, for example, a seizure, which can present as an apparent syncope event. Further, glucose concentration recorded by a glucose sensor would be temporally matched to the monitoring ECG data and aid in distinguishing metabolic events, including hypoglycemia, which can present as an apparent syncope, from true syncope. In addition, recording a patient's airflow in tandem with a syncope event may also aid in distinguishing a hyperventilation metabolic event from a true syncope event. Optionally, these other physiological data may be processed according to diagnostic and prognostic values of the data (step 164).

Following the optional processing of other contemporaneous data, the type of syncope event can also be detected optionally (step 165), as further described with reference to FIG. 25. As cardiac-based syncope is associated with the highest mortality rate, the distinction between cardiac-based syncope and both non-cardiac-based syncope events as well as apparent syncope events that are not true syncope, such as seizures, hypoglycemia, and hyperventilation, is an important distinction. Where an abnormal ECG baseline is recorded contemporaneous with a syncope event, cardiac-based syncope is highly likely. For example, a prolonged QT interval and non-sustained polymorphic ventricular tachycardia concurrent to a syncopal event may indicate Long QT Syndrome; whereas a concurrent short PR interval, delta wave, and syncopal event suggests Wolffe-Parkinson-White syndrome; syncope contemporaneous with a right bundle branch block pattern and ST segment elevation indicates Brugada syndrome; syncope in tandem with a PR interval that is not followed by a QRS complex may indicate a high-grade AV block; and syncope paired with a T-wave inversion may suggest ischemia or cardiomyopathy. Thus, after other physiological data are processed, the ECG data that are contemporaneous to the syncope event are analyzed, and the method 160 determines whether the type of syncope event (step 165), as further described with reference to FIG. 25. Finally, the syncope event information as well as approximately concurrent ECG and other physiological data is output to a user, such as a physician, such as though a screen of a personal computer 129 (step 166). The output information can include the time the events occurred, the duration of the events, the type of the event (for example, cardiac-based or non-cardiac-based syncope), the magnitude of the syncope abnormality during the event, and information about the identified concurrent ECG and other physiological data. Any events identified based on the ECG and other physiological data can also be output to the user. In a further embodiment, ECG and other physiological data that is not substantially contemporaneous to the syncope events is also output to the user. Still other operations and steps are possible. Other types of processing the other physiological data are possible.

Figure 25:
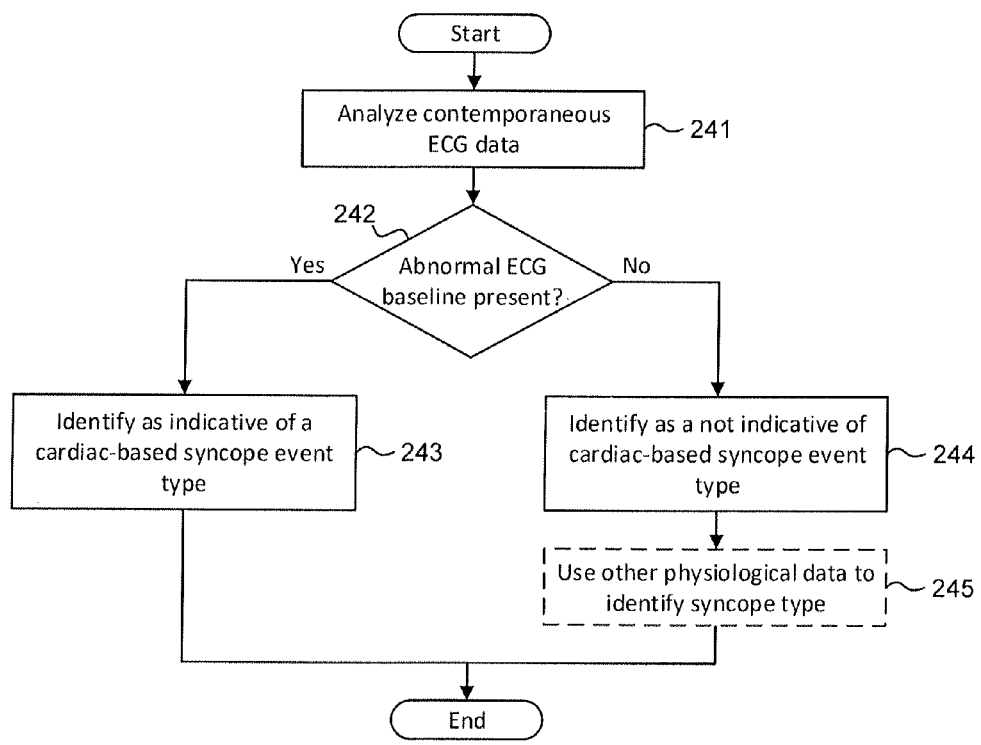
FIG. 25 is a flow diagram showing a routine for identifying a type of a syncope event for use in the method of FIG. 16 in accordance with one embodiment.

FIG. 25 is a flow diagram showing a routine 240 for identifying a type of a syncope event for use in the method of FIG. 16 in accordance with one embodiment. ECG data contemporaneous to the identified syncope event is analyzed (step 241). Where an abnormal ECG baseline is present (step 242), the syncope event is identified as indicative of a cardiac-based syncope event (step 243), but where an abnormal baseline is not present (step 242), the syncope event is identified not indicative of a cardiac-based syncope event (step 244). Optionally, routine 240 proceeds to step 245, where the routine 240 then uses any additional physiological data to determine the type syncope event, such as non-cardiac, apparent syncope that is due to low glucose. Apparent syncope due to low glucose may be diagnosed through recording a low blood glucose concentration concurrent with apparent syncope. A second example of additional physiological data that may aid in diagnosing syncope is respiratory data; respiratory data that suggest hyperventilation and are concurrent with apparent syncope data may indicate a metabolic, hyperventilation basis for apparent syncope. Still other embodiments are possible.

Moreover, as indicated supra, many embodiments for the patch and monitor are also possible. Conventional ECG monitors, such as Holter monitors, invariably require specialized training on proper placement of leads and on the operation of recording apparatuses, plus support equipment purpose-built to retrieve, convert, and store ECG monitoring data. In contrast, the wearable monitor 12 simplifies monitoring from end to end, beginning with placement, then with use, and, finally, with data retrieval. FIGS. 23A-C are functional block diagrams, respectively, showing practical uses 210, 220, 230 for the wearable monitors 12 of FIGS. 1 and 2. The combination of a flexible extended wear electrode patch and a removable reusable (or single use) monitor recorder empowers physicians and patients with the ability to readily perform long-term ambulatory ECG, syncope, and physiology monitoring.

Especially compared with existing Holter-type monitors and monitoring patches placed in the upper pectoral region, the wearable monitor 12 offers superior patient comfort as well as convenience and is user-friendly. First, the electrode patch 15 is specifically designed for ease of use by a patient (or caregiver); assistance by professional medical personnel is not required. Moreover, the patient is free to replace the electrode patch 15 at any time and need not wait for a doctor's appointment to have a new electrode patch 15 placed. In addition, the monitor recorder 14 operates automatically, and the patient only need snap the monitor recorder 14 into place on the electrode patch 15 to initiate ECG monitoring. Thus, based on the synergistic combination of the electrode patch 15 and monitor recorder 14, using the wearable monitor 12 is a reliable and virtually foolproof way to monitor a patient's ECG, syncope, and physiology for an extended, or even open-ended, period of time.

Figure 24A:
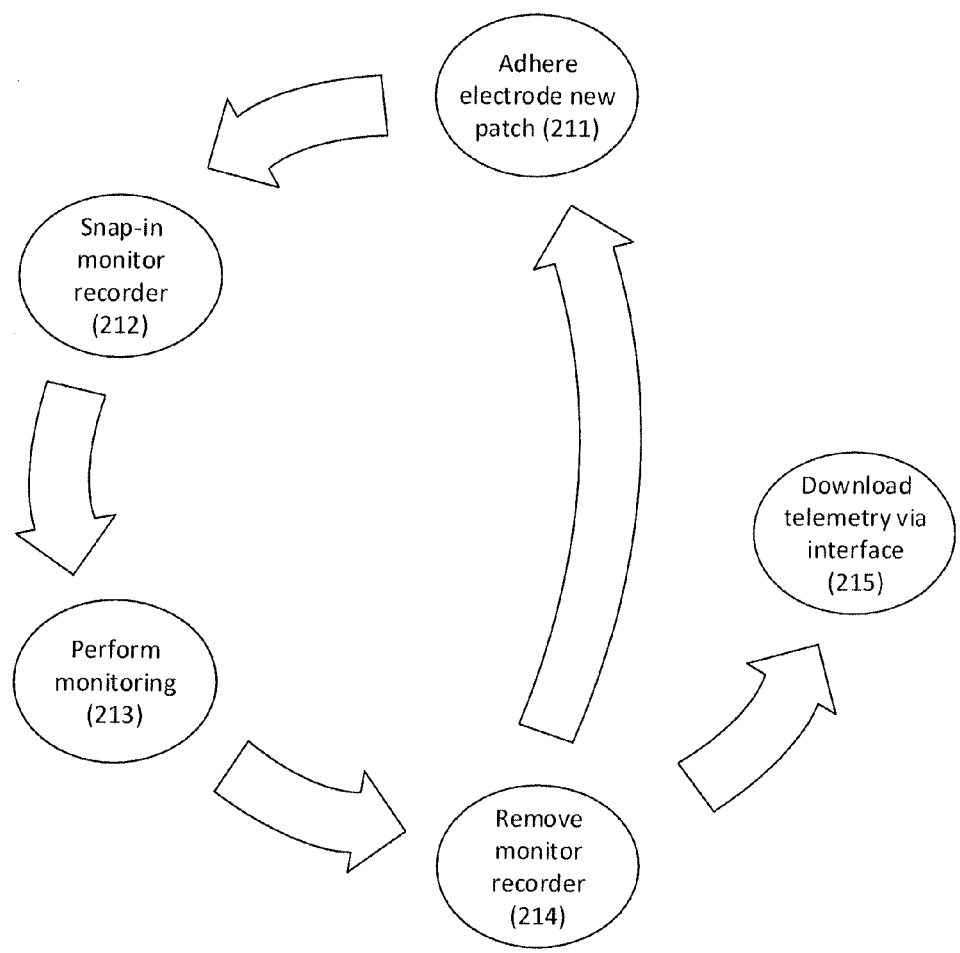
FIGS. 24A-C are functional block diagrams respectively showing practical uses of the ambulatory extended-wear electrocardiography and syncope sensor monitors of FIGS. 1 and 2.

In simplest form, extended wear monitoring can be performed using the same monitor recorder 14 inserted into a succession of fresh new electrode patches 15. As needed, the electrode patch 15 can be replaced by the patient (or caregiver) with a fresh new electrode patch 15 throughout the overall monitoring period. Referring first to FIG. 24A, at the outset of monitoring, a patient adheres a new electrode patch 15 in a location at the sternal midline 16 (or immediately to either side of the sternum 13) oriented top-to-bottom (step 211). The placement of the wearable monitor in a location at the sternal midline (or immediately to either side of the sternum), with a unique narrow "hourglass"-like shape, significantly improves the ability of the wearable monitor to cutaneously sense cardiac electrical potential signals, particularly the P-wave (or atrial activity) and, to a lesser extent, the QRS interval signals that indicate ventricular activity in the ECG waveforms.

Placement involves simply adhering the electrode patch 15 on the skin along the sternal midline 16 (or immediately to either side of the sternum 13). Patients can easily be taught to find the physical landmarks on the body necessary for proper placement of the electrode patch 15. The physical landmarks are locations on the surface of the body that are already familiar to patients, including the inter-mammary cleft between the breasts above the manubrium (particularly easily locatable by women and gynecomastic men), the sternal notch immediately above the manubrium, and the Xiphoid process located at the bottom of the sternum. Empowering patients with the knowledge to place the electrode patch 15 in the right place ensures that the ECG electrodes will be correctly positioned on the skin, no matter the number of times that the electrode patch 15 is replaced.

A monitor recorder 14 is snapped into the non-conductive receptacle 25 on the outward-facing surface of the electrode patch 15 (step 212). The monitor recorder 14 draws power externally from a battery provided in the non-conductive receptacle 25. In addition, the battery is replaced each time that a fresh new electrode patch 15 is placed on the skin, which ensures that the monitor recorder 14 is constantly operating with a fresh power supply and minimizes the chances of a loss of monitoring continuity due to a depleted battery source.

By default, the monitor recorder 14 automatically initiates monitoring upon sensing body surface potentials through the pair of ECG electrodes (step 213). In a further embodiment, the monitor recorder 14 can be configured for manual operation, such as by using the tactile syncope feedback button 66 on the outside of the sealed housing 50 or other user-operable control. In an even further embodiment, the monitor recorder 14 can be configured for remotely-controlled operation by equipping the monitor recorder 14 with a wireless transceiver, such as described in commonly-assigned U.S. patent application, entitled "Remote Interfacing of an Extended Wear Electrocardiography and Physiological Sensor Monitor," Ser. No. 14/082,071, filed Nov. 15, 2013, pending, the disclosure of which is incorporated by reference. The wireless transceiver allows wearable or mobile communications devices to wirelessly interface with the monitor recorder 14.

A key feature of the extended wear wearable monitor 12 is the ability to monitor ECG and physiological data for an extended period of time, which can be well in excess of the 14 days currently proposed as achievable by conventional ECG monitoring approaches. In a further embodiment, ECG monitoring can even be performed over an open-ended time period, as further explained infra. The monitor recorder 14 is reusable and, if so desired, can be transferred to successive electrode patches 15 to ensure continuity in monitoring. At any point during ECG monitoring, a patient (or caregiver) can remove the monitor recorder 14 (step 214) and replace the electrode patch 15 currently being worn with a fresh new electrode patch 15 (step 211). The electrode patch 15 may need to be replaced for any number of reasons. For instance, the electrode patch 15 may begin to come off after a period of wear, or the patient may have skin that is susceptible to itching or irritation. Wearing ECG electrodes can aggravate such skin conditions. Thus, a patient may want or need to periodically remove or replace ECG electrodes during a long-term ECG monitoring period, whether to replace a dislodged electrode, reestablish better adhesion, alleviate itching or irritation, allow for cleaning the skin, allow for showering and exercise, or for other purpose.

Following replacement, the monitor recorder 14 is again snapped into the electrode patch 15 (step 212) and monitoring resumes (step 213). The ability to transfer the same monitor recorder 14 to successive electrode patches 15 during a period of extended wear monitoring is advantageous, not only for diagnosing cardiac rhythm disorders and other physiological events of potential concern, but also for extremely long term monitoring, such as following up on cardiac surgery, ablation procedures, or medical device implantation. In these cases, several weeks of monitoring or more may be needed. In addition, certain IMDs, such as pacemakers or implantable cardioverter defibrillators, incorporate a loop recorder that will capture cardiac events over a fixed time window. If the telemetry recorded by the IMD is not downloaded in time, cardiac events that occurred at a time preceding the fixed time window will be overwritten by the IMD and, therefore, lost. The monitor recorder 14 provides continuity of monitoring that acts to prevent loss of cardiac event data. In a further embodiment, the firmware executed by the microcontroller 61 of the monitor recorder 14 can be optimized for minimal power consumption and additional flash memory for storing monitoring data can be added to produce a multi-week monitor recorder 14 that can be snapped into a fresh new electrode patch 15 every seven days, or other interval, for weeks or even months.

Upon the conclusion of monitoring, the monitor recorder 14 is removed (step 214), and the recorded ECG and physiological telemetry are downloaded (step 215). For instance, a download station can be physically interfaced to the external connector 65 of the monitor recorder 14 to initiate and conduct downloading, as described supra with reference to FIG. 18.

Figure 24B:
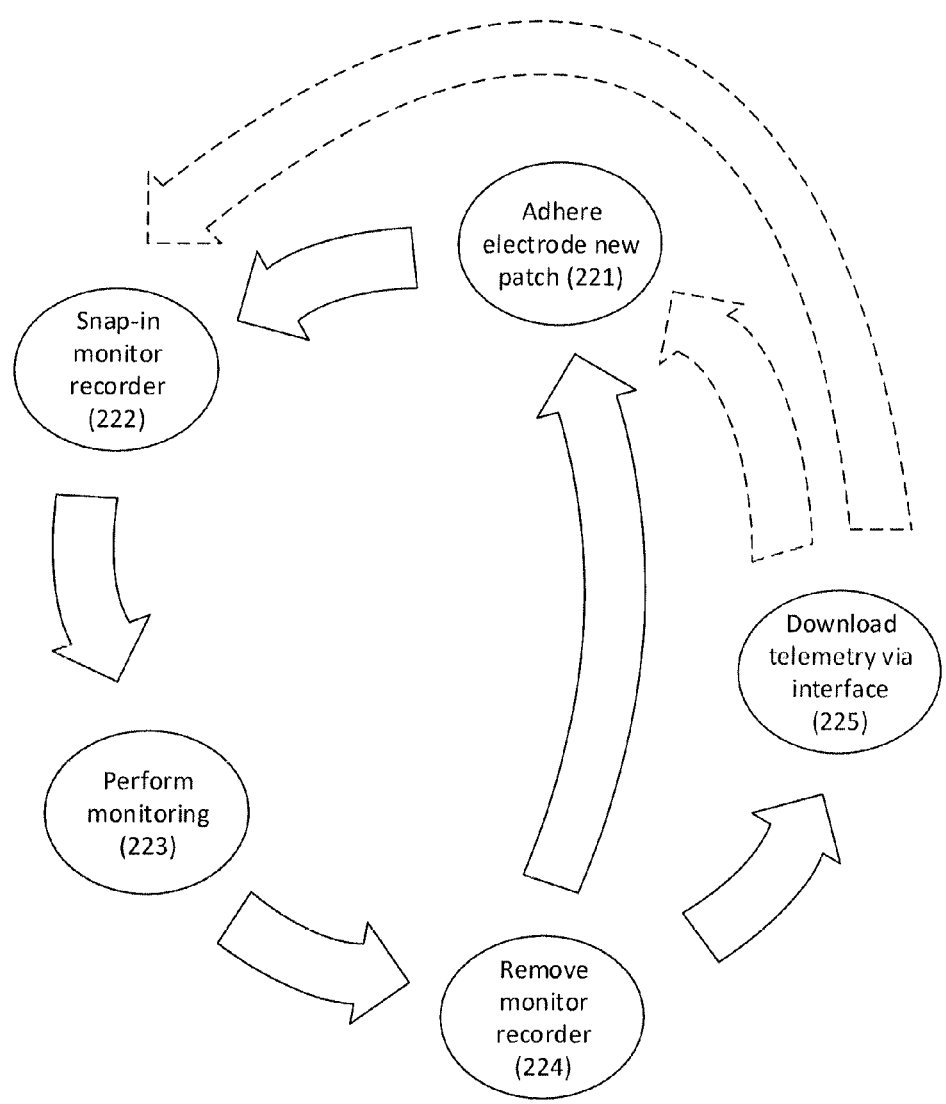

In a further embodiment, the monitoring period can be of indeterminate duration. Referring next to FIG. 24B, a similar series of operations are followed with respect to replacement of electrode patches 15, reinsertion of the same monitor recorder 14, and eventual download of ECG and physiological telemetry (steps 221-225), as described supra with reference to FIG. 24A. However, the flash memory 62, as further described with reference to FIG. 9, in the circuitry 60 of the monitor recorder 14 has a finite capacity. Following a successful download of stored data, the flash memory 62 can be cleared to restore storage capacity, and monitoring can resume, either by first adhering a new electrode patch 15 (step 221) or by snapping the monitor recorder 14 into an already-adhered electrode patch 15 (step 222). The foregoing expanded series of operations to include reuse of the same monitor recorder 14 following data download, which allows monitoring to continue indefinitely without the types of interruptions that often affect conventional approaches, including retrieving monitoring data only through making an appointment with a medical professional.

Figure 24C:
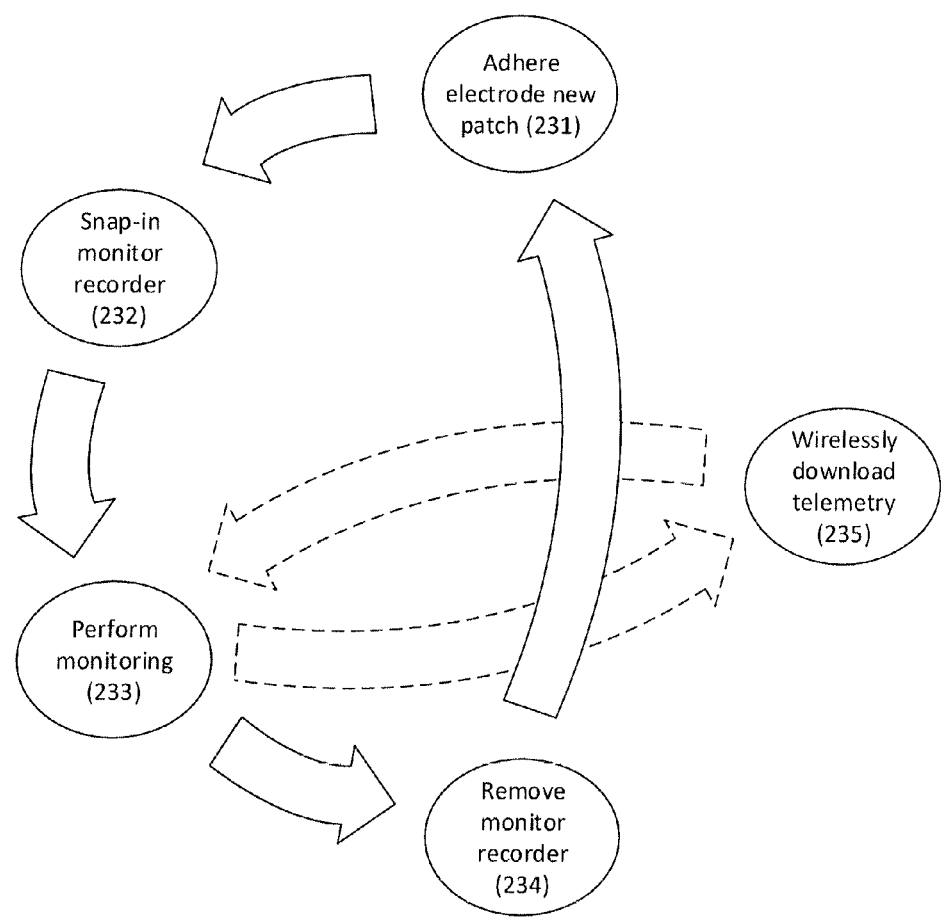

In a still further embodiment, when the monitor recorder 14 is equipped with a wireless transceiver, the use of a download station can be skipped. Referring last to FIG. 24C, a similar series of operations are followed with respect to replacement of electrode patches 15 and reinsertion of the same monitor recorder 14 (step 231-234), as described supra with reference to FIG. 24A. However, recorded ECG and physiological telemetry are downloaded wirelessly (step 235), such as described in commonly-assigned U.S. patent application Ser. No. 14/082,071, cited supra. The recorded ECG and physiological telemetry can even be downloaded wirelessly directly from a monitor recorder 14 during monitoring while still snapped into the non-conductive receptacle 25 on the electrode patch 15. The wireless interfacing enables monitoring to continue for an open-ended period of time, as the downloading of the recorded ECG and physiological telemetry will continually free up onboard storage space. Further, wireless interfacing simplifies patient use, as the patient (or caregiver) only need worry about placing (and replacing) electrode patches 15 and inserting the monitor recorder 14. Still other forms of practical use of the extended wear electrocardiography monitors 12 are possible.

Figure 19:
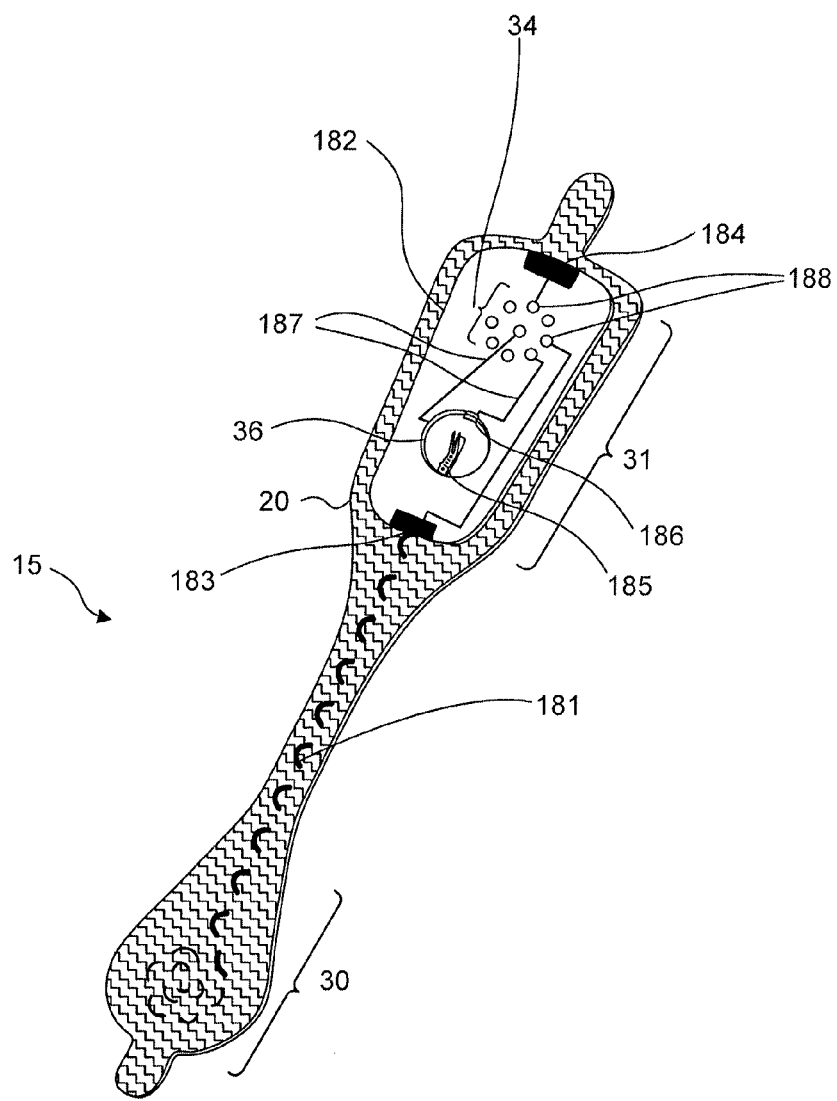
FIG. 19 is a perspective view of an extended wear electrode patch with a flexile wire electrode assembly in accordance with a still further embodiment.

The circuit trace and ECG electrodes components of the electrode patch 15 can be structurally simplified. In a still further embodiment, the flexible circuit 32, as further described with reference to FIG. 5, and distal ECG electrode 38 and proximal ECG electrode 39, as further described with reference to FIG. 6, are replaced with a pair of interlaced flexile wires. Interlacing of flexile wires through the flexible backing 20 reduces both manufacturing costs and environmental impact, as further described infra. The flexible circuit and ECG electrodes are replaced with a pair of flexile wires that serve as both electrode circuit traces and electrode signal pickups. FIG. 19 is a perspective view 180 of an extended wear electrode patch 15 with a flexile wire electrode assembly in accordance with a still further embodiment. The flexible backing 20 maintains the unique narrow "hourglass"-like shape that aids long term extended wear, particularly in women, as described supra with reference to FIG. 4. For clarity, the non-conductive receptacle 25 is omitted to show the exposed battery printed circuit board 182 that is adhered underneath the non-conductive receptacle 25 to the proximal end 31 of the flexible backing 20. Instead of employing flexible circuits, a pair of flexile wires are separately interlaced or sewn into the flexible backing 20 to serve as circuit connections for an anode electrode lead and for a cathode electrode lead.

To form a distal electrode assembly, a distal wire 181 is interlaced into the distal end 30 of the flexible backing 20, continues along an axial path through the narrow longitudinal midsection of the elongated strip, and electrically connects to the battery printed circuit board 182 on the proximal end 31 of the flexible backing 20. The distal wire 181 is connected to the battery printed circuit board 182 by stripping the distal wire 181 of insulation, if applicable, and interlacing or sewing the uninsulated end of the distal wire 181 directly into an exposed circuit trace 183. The distal wire-to-battery printed circuit board connection can be made, for instance, by back stitching the distal wire 181 back and forth across the edge of the battery printed circuit board 182. Similarly, to form a proximal electrode assembly, a proximal wire (not shown) is interlaced into the proximal end 31 of the flexible backing 20. The proximal wire is connected to the battery printed circuit board 182 by stripping the proximal wire of insulation, if applicable, and interlacing or sewing the uninsulated end of the proximal wire directly into an exposed circuit trace 184. The resulting flexile wire connections both establish electrical connections and help to affix the battery printed circuit board 182 to the flexible backing 20.

The battery printed circuit board 182 is provided with a battery compartment 36. A set of electrical pads 34 are formed on the battery printed circuit board 182. The electrical pads 34 electrically interface the battery printed circuit board 182 with a monitor recorder 14 when fitted into the non-conductive receptacle 25. The battery compartment 36 contains a spring 185 and a clasp 186, or a similar assembly, to hold a battery (not shown) in place and electrically interfaces the battery with the electrical pads 34 through a pair battery leads 187 to power the electrocardiography monitor 14. Other types of battery compartment are possible. The battery contained within the battery compartment 36 can be replaceable, rechargeable, or disposable.

In a further embodiment, the circuit board and non-conductive receptacle 25 are replaced by a combined housing that includes a battery compartment and a plurality of electrical pads. The housing can be affixed to the proximal end of the elongated strip through the interlacing or sewing of the flexile wires or other wires or threads.

The core of the flexile wires may be constructed from a solid, stranded, or braided conductive metal or metal compounds. In general, a solid wire will be less flexible than a stranded wire with the same total cross-sectional area, but will provide more mechanical rigidity than the stranded wire. The conductive core may be copper, aluminum, silver, or other material. The pair of the flexile wires may be provided as insulated wire. In one embodiment, the flexile wires are constructed from a magnet wire from Belden Cable, catalogue number 8051, with a solid core of AWG 22, bare copper as conductor material, and insulation using polyurethane or nylon. Still other types of flexile wires are possible. In a further embodiment, conductive ink or graphene can be used to print electrical connections, either in combination with or in place of the flexile wires.

Figure 20:
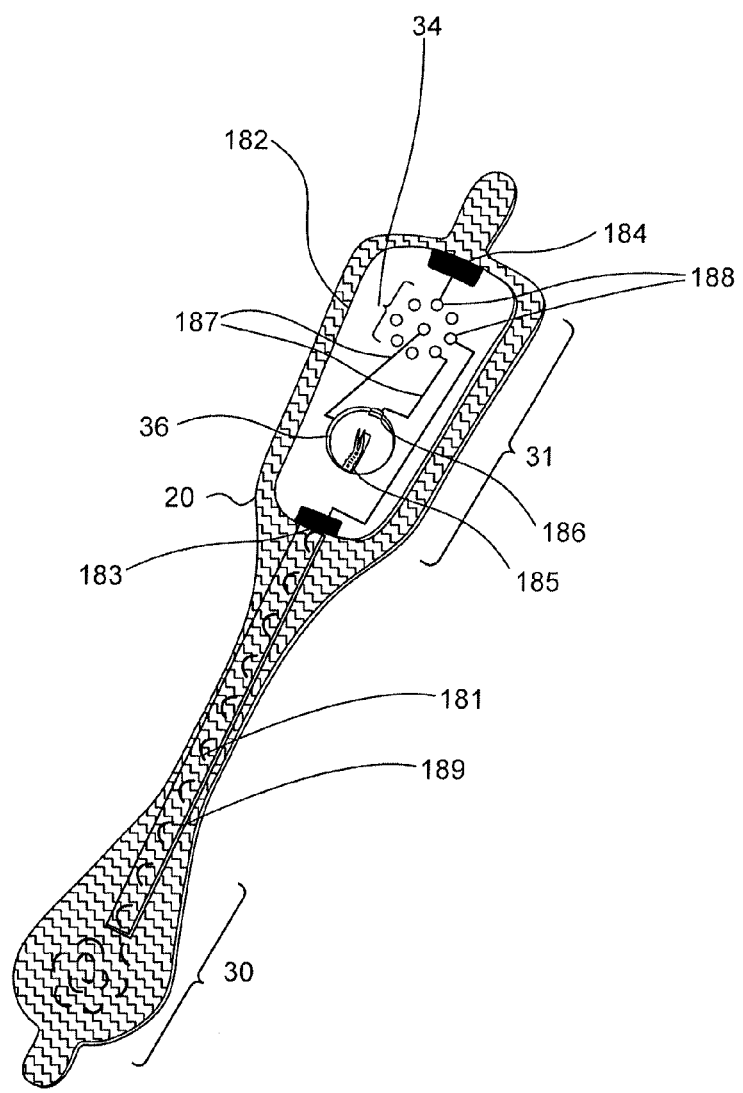
FIG. 20 is perspective view of the flexile wire electrode assembly from FIG. 19, with a layer of insulating material shielding a bare distal wire around the midsection of the flexible backing.

In a still further embodiment, the flexile wires are uninsulated. FIG. 20 is perspective view of the flexile wire electrode assembly from FIG. 19 with a layer of insulating material 189 shielding a bare uninsulated distal wire 181 around the midsection on the contact side of the flexible backing. On the contact side of the proximal and distal ends of the flexible backing, only the portions of the flexile wires that serves as electrode signal pickups are electrically exposed, and the remaining flexile wire on the contact side outside of the proximal and distal ends is shielded from electrical contact. The bare uninsulated distal wire 181 may be insulated using a layer of plastic, rubber-like polymers, or varnish, or by an additional layer of gauze or adhesive (or non-adhesive) gel. The bare uninsulated wire 181 on the non-contact side of the flexible backing may be insulated or simply remain uninsulated.

Figure 21:
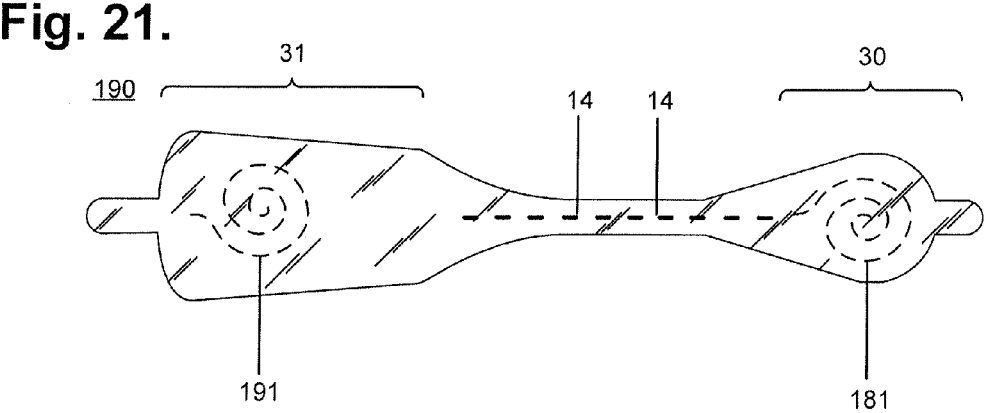
FIG. 21 is a bottom view of the flexile wire electrode assembly as shown in FIG. 19.

Both end portions of the pair of flexile wires are typically placed uninsulated on the contact surface of the flexible backing 20 to form a pair of electrode signal pickups. FIG. 21 is a bottom view 190 of the flexile wire electrode assembly of FIG. 19. When adhered to the skin during use, the uninsulated end portions of the distal wire 181 and the proximal wire 191 enable the monitor recorder 14 to measure dermal electrical potential differentials. At the proximal and distal ends of the flexible backing 20, the uninsulated end portions of the flexile wires may be configured into an appropriate pattern to provide an electrode signal pickup, which would typically be a spiral shape formed by guiding the flexile wire along an inwardly spiraling pattern. The surface area of the electrode pickups can also be variable, such as by selectively removing some or all of the insulation on the contact surface. For example, an electrode signal pickup arranged by sewing insulated flexile wire in a spiral pattern could have a crescent-shaped cutout of uninsulated flexile wire facing towards the signal source.

Figure 22:
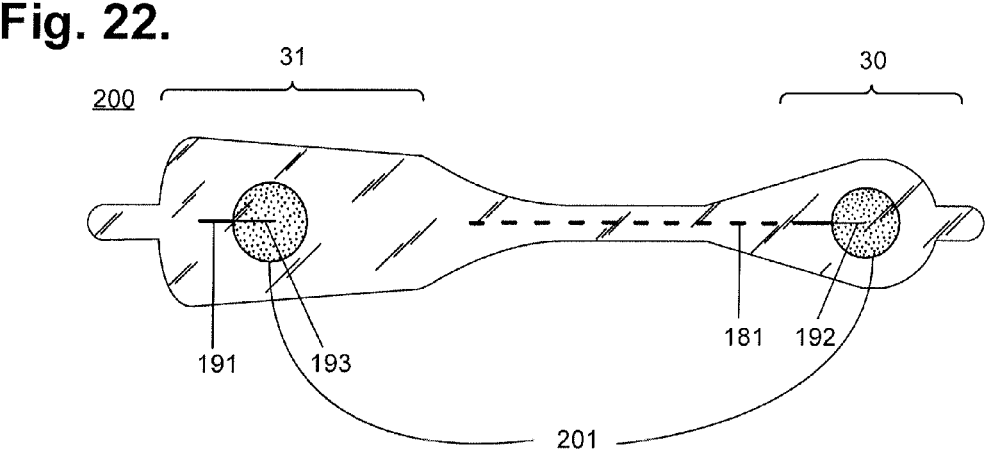
FIG. 22 is a bottom view of a flexile wire electrode assembly in accordance with a still yet further embodiment.

In a further embodiment, the flexile wires remain freely riding on the contact surfaces on the distal and proximal ends of the flexible backing, rather than being interlaced into the ends of the flexible backing 20. FIG. 22 is a bottom view 200 of a flexile wire electrode assembly in accordance with a still yet further embodiment. The distal wire 181 is interlaced onto the midsection and extends an exposed end portion 192 onto the distal end 30. The proximal wire 191 extends an exposed end portion 193 onto the proximal end 31. The exposed end portions 192 and 193, which are not shielded with insulation, are further embedded within an electrically conductive adhesive 201. The adhesive 201 makes contact to skin during use and conducts skin electrical potentials to the monitor recorder 14 (not shown) via the flexile wires. The adhesive 201 can be formed from electrically conductive, non-irritating adhesive, such as hydrocolloid.

Figure 23:
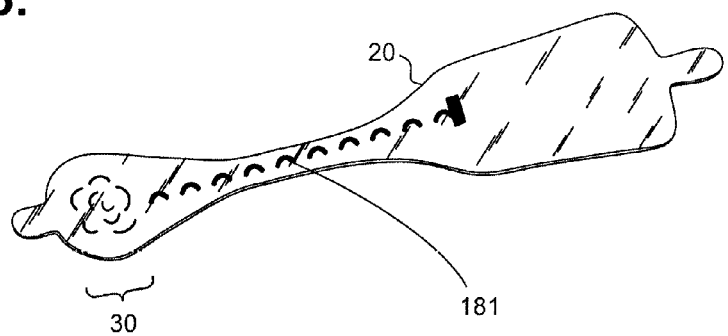
FIG. 23 is a perspective view showing the longitudinal midsection of the flexible backing of the electrode assembly from FIG. 19.

The distal wire 181 is interlaced or sewn through the longitudinal midsection of the flexible backing 20 and takes the place of the flexible circuit 32. FIG. 23 is a perspective view showing the longitudinal midsection of the flexible backing of the electrode assembly of FIG. 19. Various stitching patterns may be adopted to provide a proper combination of rigidity and flexibility. In the simplest form, the distal wire 181 can be manually threaded through a plurality of holes provided at regularly-spaced intervals along an axial path defined between the battery printed circuit board 182 (not shown) and the distal end 30 of the flexible backing 20. The distal wire 181 can be threaded through the plurality of holes by stitching the flexile wire as a single "thread." Other types of stitching patterns or stitching of multiple "threads" could also be used, and a sewing machine or similar device can be used to machine-stitch the distal wire 181 into place, as further described infra. Further, the path of the distal wire 181 need not be limited to a straight line from the distal to the proximal end of the flexible backing 20.

While the invention has been particularly shown and described as referenced to the embodiments thereof, those skilled in the art will understand that the foregoing and other changes in form and detail may be made therein without departing from the spirit and scope.

What is claimed is:

1. An electrocardiography and syncope monitoring system, comprising:
   an ambulatory, extended-wear electrocardiography and syncope sensor monitor recorder, comprising:
      a sealed housing adapted to be removably secured into a non-conductive receptacle on a disposable extended wear electrode patch; and
      an electronic circuitry comprised within the sealed housing, comprising:
         an externally-powered, low-power microcontroller that is operable to execute under microprogrammable control as specified in a firmware;
         an electrocardiographic front end circuit electrically interfaced to the microcontroller and operable to sense electrocardiographic signals through electrocardiographic electrodes provided on the disposable extended wear electrode patch, each of the electrocardiographic electrodes adapted to be positioned axially along a midline of a sternum for capturing action potential propagation, the electrocardiographic front end circuit further operable to process the sensed electrocardiographic signals prior to storing samples of the processed signals, the processing comprising:
            amplifying, via a unity gain amplifier comprised in the electrocardiographic front end circuit, current of the electrocardiographic signals; and
            after the amplification of the current, amplifying voltage of the electrocardiographic signals while conditioning the electrocardiographic signals;
         a reference generator comprising a pair of resistors configured to receive power supply noise and system noise and to inject a driven reference containing the power supply noise and the system noise into a patient;
         a syncope sensor electrically interfaced with the microcontroller and operable to sense syncope events; and
         an externally-powered flash memory electrically interfaced with the microcontroller and operable to store the samples of the processed electrocardiographic signals the syncope events.

2. A system according to claim 1, wherein:
   the syncope sensor comprises an actigraphy-based syncope sensor assembly sensing actigraphy data, applying actigraphy filtering criteria to the sensed actigraphy data, identifying a portion of the actigraphy data indicative of the syncope events based on the actigraphy filtering criteria application and detecting the syncope events based on the portion of the data, providing the detected syncope event to the microcontroller, wherein the microcontroller stores the syncope events into the memory.

3. A system according to claim 2, wherein the syncope events comprise at least one of a falling event and a postural change and the syncope sensor further comprises a patient-mediated tactile feedback syncope button.

4. A system according to claim 2, wherein the actigraphy filtering criteria comprise a threshold of acceleration or deceleration of the sealed housing.

5. A system according to claim 2, further comprising:
a three-axis accelerometer comprised in the actigraphy-based syncope sensor assembly.

6. A system according to claim 1, further comprising:
a server computer system centrally accessible over a data communications network and comprising a processor configured to execute program code stored in a memory, the server computer system configured to:
retrieve the samples of the electrocardiographic signals and the syncope event data from the flash memory of the electronic circuitry;
identify those samples of the electrocardiographic signals that were sensed substantially concurrent to one of the sensed syncope events; and
output the samples of the syncope event data and the identified electrocardiographic signals.

7. A system according to claim 6, the server computer system further configured to:
detect whether an abnormal electrocardiography baseline is associated with a syncope event based on the electrocardiographic signals; and
determine that the syncope event is indicative of one of a cardiac-based syncope type and a non-cardiac-based syncope type based on whether the abnormal baseline is associated with detection of at least one syncope event.

8. A system according to claim 6, further comprising at least one additional sensor located at least one in the monitor recorder and the disposable patch and configured to collect physiological data comprising one or more of $SpO_2$, blood pressure, temperature, glucose level, air flow, and volumetric pressure, wherein the server computer system further configured to:
retrieve at least one of a physiological sample selected from the group comprising the $SpO_2$, the blood pressure, the temperature, the glucose level, the air flow, and the volumetric pressure;
identify those physiological samples that were sensed substantially concurrent to a time of a syncope event; and
output the syncope events and the physiological samples that were identified.

9. A system according to claim 1, the processing further comprising:
reducing high frequency noise in the electrocardiographic signals prior to the amplification of the current;
applying a high pass filter to the electrocardiographic signals with the amplified current prior to the amplification of the voltage; and
applying an anti-aliasing low-pass filter to the electrocardiographic signals with the amplified voltage,
wherein the conditioning comprises applying a low-pass filter.

10. A system according to claim 1, further comprising:
an analog-to-digital converter operable to convert the electrocardiographic signals into digital representations of cardiac activation wave front amplitudes;
at least one low-pass filter comprised in the firmware; and
at least one high-pass filter comprised in the firmware,
wherein the cardiac activation wave front amplitudes are passed through at least one low-pass filter and at least one high-pass filter following conversion into the digital representations.

11. A system according to claim 10, the microcontroller further comprising:
a compression algorithm comprised in the firmware,
wherein the cardiac activation wave front amplitudes are compressed with the compression algorithm into compressed digital representations prior to being stored in the flash memory of the electronic circuitry.

12. An electrocardiography and syncope monitoring system optimized for capturing low amplitude cardiac action potential propagation, comprising:
an ambulatory, extended-wear electrocardiography and syncope sensor monitor optimized for capturing low amplitude cardiac action potential propagation, comprising:
a disposable extended wear electrode patch comprising:
a flexible backing formed of an elongated strip of stretchable material with a narrow longitudinal midsection and, on each end, a contact surface at least partially coated with an adhesive dressing provided as a crimp relief, the elongated strip being narrower at the longitudinal midsection than at the ends;
a pair of electrocardiographic electrodes conductively exposed on the contact surface of each end of the elongated strip;
a non-conductive receptacle adhered to an outward-facing end of the elongated strip and comprising a plurality of electrical pads; and
a flexible circuit affixed on each end of the elongated strip as a strain relief and comprising a pair of circuit traces electrically coupled to the pair of electrocardiographic electrodes and a pair of the electrical pads; and
a battery electrically interfaced to a different pair of the pads; and
a sealed housing adapted to be removably secured into a non-conductive receptacle on a disposable extended wear electrode patch; and
an electronic circuitry comprised within the sealed housing, comprising:
a low-power microcontroller that is operable to draw power from the battery via the different pair of the electrical pads and that is operable to execute under microprogrammable control as specified in a firmware;
an electrocardiographic front end circuit electrically interfaced to the microcontroller and operable to sense electrocardiographic signals through electrocardiographic electrodes provided on the disposable extended wear electrode patch, each of the electrocardiographic electrodes adapted to be positioned axially along a midline of a sternum for capturing action potential propagation; and
a syncope sensor electrically interfaced with the microcontroller and operable to sense syncope events, the syncope sensor comprising an actigraphy-based syncope sensor sensing actigraphy data, applying actigraphy filtering criteria to the sensed actigraphy data, identifying a portion of the actigraphy data indicative of the syncope events based on the actigraphy filtering criteria application and detecting the syncope events based on the portion of the data, providing the detected syncope event to the microcontroller, wherein the microcontroller stores the syncope events into the memory; and a flash memory electrically interfaced with the microcontroller and operable to store samples of the electrocardiographic signals and the syncope events, the memory further operable to draw power from the battery via the different pair of the electrical pads.

13. A system according to claim 12, wherein the syncope sensor further comprises a patient-mediated tactile feedback syncope button.

14. A system according to claim 12, wherein the syncope events comprise at least one of a falling event and a postural change event.

15. A system according to claim 12, wherein the actigraphy filtering criteria comprise a threshold of acceleration or deceleration of the sealed housing.

16. A system according to claim 12, further comprising:
a server computer system centrally accessible over a data communications network and comprising a processor configured to execute program code stored in a memory, the server configured to:
retrieve the samples of the electrocardiographic signals and the syncope event data from the flash memory of the electronic circuitry;
identify those samples of the electrocardiographic signals that were sensed substantially concurrent to one of the syncope events; and
output the samples of the syncope event data and the identified electrocardiographic signals.

17. A system according to claim 16, the server computer system further configured to:
detect whether an abnormal electrocardiography baseline is associated with a syncope event based on the electrocardiographic signals; and
determine that the syncope event is indicative of one of a cardiac-based syncope type and a non-cardiac-based syncope type based on whether the abnormal baseline is associated with detection of at least one syncope event.

18. A system according to claim 12, wherein the electrocardiographic front end circuit is further operable to:
reduce high frequency noise in the sensed electrocardiographic signals;
amplify current of the sensed electrocardiographic signals in which the high-frequency noise is reduced;
apply a high pass filter to the sensed electrocardiographic signals with the amplified current;
amplify voltage of the filtered electrocardiographic signals while applying a low-pass filter to the filtered electrocardiographic signals; and
apply an anti-aliasing low-pass filter to the electrocardiographic signals with the amplified voltage.

19. A system according to claim 12, further comprising:
an analog-to-digital converter operable to convert the electrocardiographic signals into digital representations of cardiac activation wave front amplitudes;
at least one low-pass filter comprised in the firmware; and
at least one high-pass filter comprised in the firmware,
wherein the cardiac activation wave front amplitudes are passed through at least one low-pass filter and at least one high-pass filter following conversion into the digital representations.

20. A system according to claim 19, the microcontroller further comprising:
a compression algorithm comprised in the firmware,
wherein the cardiac activation wave front amplitudes are compressed with the compression algorithm into compressed digital representations prior to being stored in the flash memory of the electronic circuitry.

* * * * *